(12) United States Patent
Echevarria Vallespi et al.

(10) Patent No.: US 11,830,110 B2
(45) Date of Patent: *Nov. 28, 2023

(54) AUTHORING AND OPTIMIZATION OF ACCESSIBLE COLOR THEMES

(71) Applicant: ADOBE INC., San Jose, CA (US)

(72) Inventors: Jose Ignacio Echevarria Vallespi, South San Francisco, CA (US); Adrian Cristian Brojbeanu, Ilfov (RO); Bernard James Kerr, Sausalito, CA (US)

(73) Assignee: Adobe Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,568

(22) Filed: Aug. 9, 2022

(65) Prior Publication Data

US 2022/0383560 A1 Dec. 1, 2022

Related U.S. Application Data

(62) Division of application No. 16/682,988, filed on Nov. 13, 2019, now Pat. No. 11,450,035.

(51) Int. Cl.
```
G06T 11/00      (2006.01)
A61B 3/06       (2006.01)
G09B 21/00      (2006.01)
G09B 5/02       (2006.01)
G09B 5/06       (2006.01)
G09G 5/06       (2006.01)
```

(52) U.S. Cl.
CPC ............ *G06T 11/001* (2013.01); *A61B 3/066* (2013.01); *G09B 5/02* (2013.01); *G09B 5/06* (2013.01); *G09B 21/008* (2013.01); *G09G 5/06* (2013.01)

(58) Field of Classification Search
None
See application file for complete search history.

(56) References Cited

U.S. PATENT DOCUMENTS

| | | | |
|---|---|---|---|
| 10,319,116 B1 | 6/2019 | C et al. | |
| 11,450,035 B2 | 9/2022 | Echevarria Vallespi et al. | |
| 2003/0174866 A1 | 9/2003 | Poynter | |
| 2004/0212815 A1 | 10/2004 | Heeman et al. | |
| 2005/0111019 A1 | 5/2005 | Nakauchi et al. | |
| 2006/0015571 A1 | 1/2006 | Fukuda et al. | |
| 2006/0132871 A1* | 6/2006 | Beretta | H04N 1/62 358/518 |
| 2012/0147163 A1 | 6/2012 | Kaminsky | |
| 2017/0290504 A1 | 10/2017 | Khaderi et al. | |
| 2017/0301310 A1 | 10/2017 | Bonnier et al. | |

* cited by examiner

*Primary Examiner* — Aaron M Richer
(74) *Attorney, Agent, or Firm* — Shook, Hardy & Bacon L.L.P.

(57) ABSTRACT

Embodiments of the present disclosure relate to computer storage, methods, and systems for the optimization of accessible color themes. Systems and methods are disclosed that leverage the use of confusion lines to identify and highlight relationships between colors that may be inaccessible (e.g., indistinguishable) for a person with a vision impairment, such as a color vision deficiency. In some embodiments, a graphical user interface is provided that, based on a selection of colors in a color wheel, visually indicates curves of confusion for each color in the selection of colors. Each curve of confusion visually indicates a confusion of colors for a type of vision impairment, such as a CVD.

17 Claims, 13 Drawing Sheets
(6 of 13 Drawing Sheet(s) Filed in Color)

AUTHORING AND OPTIMIZATION OF ACCESSIBLE COLOR THEMES

CROSS-REFERENCE TO RELATED APPLICATIONS

This application is a Divisional patent application of U.S. patent application Ser. No. 16/682,988 titled "AUTHORING AND OPTIMIZATION OF ACCESSIBLE COLOR THEMES" filed on Nov. 13, 2019, which is incorporated herein by reference in its entirety.

BACKGROUND

Color choice plays an important role in conveying certain information, as well as influencing behavior and decision-making. Color choice is particularly important in e-commerce and digital spaces (e.g., advertising, marketing, branding, promotion, website creation, data visualization, infographics, etc.) as it can impact how customers and/or users perceive content associated with, for example, an advertising campaign or a specific website. For example, color choice can influence a consumer's feelings or perception about a company's goods and services, and it can play a role in increased (or decreased) sales and/or website traffic. Oftentimes, the message and/or intent that color choice is intended to convey (e.g., pros/cons, categorization, differentiation, etc.) may be less effective for consumers and/or users affected by vision impairments. Color accessibility, that is, choosing colors and/or color combinations that are distinguishable (e.g., accessible) for those with a vision impairment, enables viewers and/or users with visual impairments to interact with content (e.g., marketing, promotions, websites, etc.) in a similar way as their non-visually-impaired counterparts. Color accessibility is particularly important for design elements in the digital space that rely on the accurate perception of color or combinations of color to convey certain information to users (e.g., using colored sections to denote differently-priced tickets on a stadium plan, using color to denote the availability or unavailability of seating at a concert venue, etc.). Traditionally, designing for color accessibility has proved challenging, as it can be difficult to imagine how content is going to be perceived by a user affected by a color vision deficiency (CVD).

SUMMARY

Embodiments of the present disclosure relate to computer storage, methods, and systems for the authoring and optimization of accessible color themes. Systems and methods are disclosed that leverage the use of confusion lines to identify and highlight relationships between colors that may be inaccessible (e.g., indistinguishable) for a person with a vision impairment, such as a color vision deficiency.

In some embodiments, a graphical user interface is provided that, based on a selection of colors in a color space (e.g., a color wheel), visually indicates curves of confusion for each color in the selection of colors. Each curve of confusion visually indicates a confusion of colors (e.g., conflicting colors; colors that will be perceived with a very similar hue) for a particular type of color vision deficiency. Each selected color may have multiple curves of confusion associated with it, including a protan curve of confusion, deutan curve of confusion, and tritan curve of confusion. As a color from the selection of colors is repositioned within the color wheel, the curves of confusion associated with that color are iteratively updated. In embodiments, when a curve of confusion associated with a first color intersects a second color selected within the color wheel, the intersection visually indicates a confusion of colors (e.g., potential color conflict) between the first color and the second color for the type of vision impairment for that curve of confusion. For example, if a protan curve of confusion associated with a selected red color intersects with a selected green color, the intersection visually indicates a conflict between the selected red color and the selected green color for a protan CVD.

In further embodiments, a given set of input colors (e.g., an ordered set or an unordered set) selected from a color wheel (or elsewhere) can be automatically optimized for color accessibility using confusion lines. The set of input colors may include color constraints denoting input colors that will remain the same, as well as identifying colors that may be updated. The set of input colors may be optimized according to (e.g., utilizing) an objective function, including at least one of a CVD alignment term, out-of-gamut term, distinguishability term, and faithfulness term. When applied to (e.g. evaluated on, optimized) the set of input colors inside an optimizer (e.g., a Nelder-Mead simplex direct search numerical method optimizer), the objective function may determine a value indicating an accessibility of the set of colors. In operation, as the value decreases, the accessibility of the set of input colors increases. Once determined, an updated (e.g., accessible) set of colors may be displayed, such as on a graphical user interface of a user device. In some embodiments, the updated set of colors may be displayed for further modification, such as, for example, by a user (e.g., content creator).

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is described in detail below with reference to the attached drawing figures, wherein.

DETAILED DESCRIPTION

Overview

Figure 1:
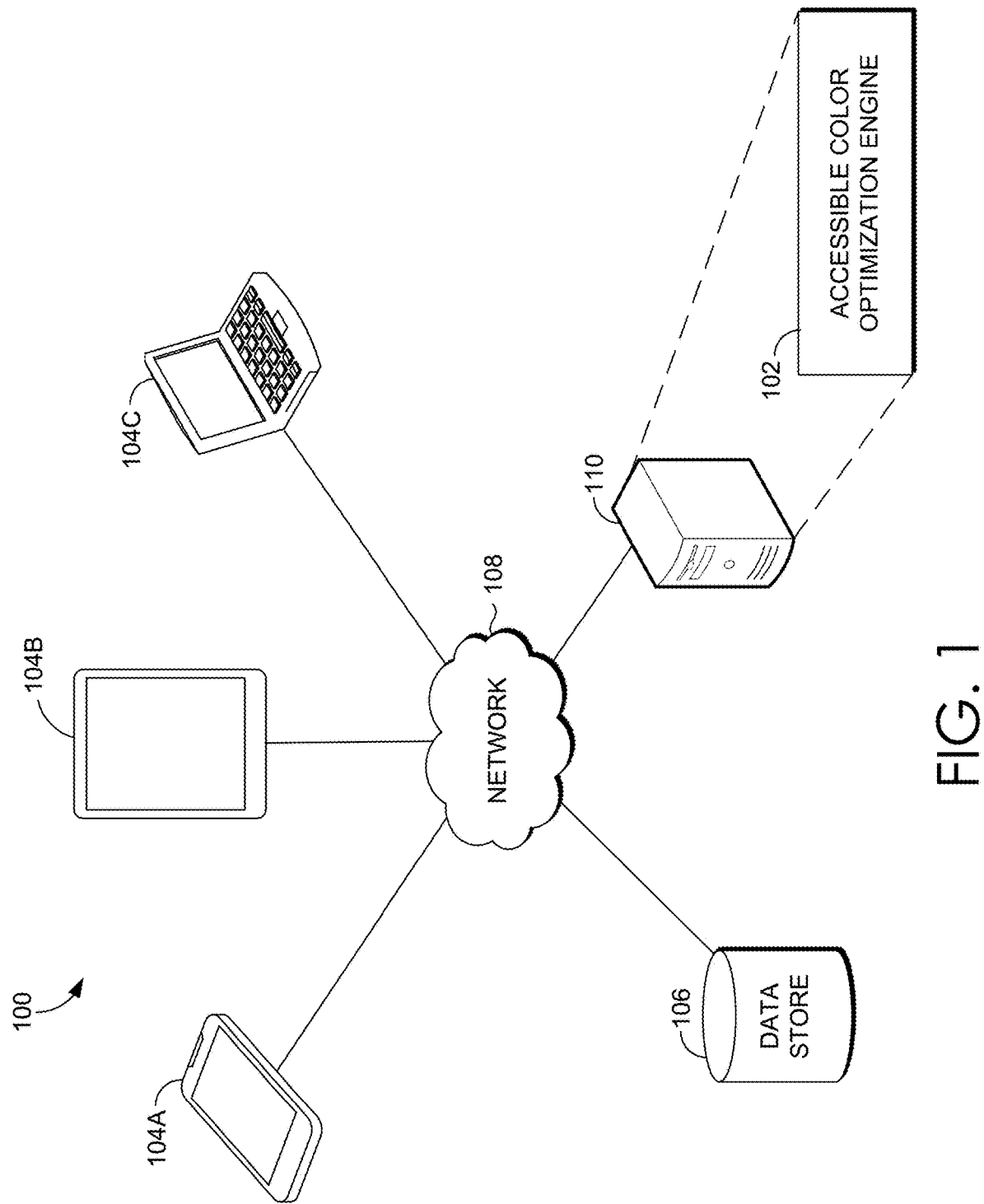
FIG. 1 is a schematic depiction of an accessible color system for optimizing for accessible colors using confusion lines, in accordance with embodiments of the present disclosure.

When used in the digital space (e.g., online marketing, advertising campaigns, promotions, website creation, etc.), color choice impacts how customers and users perceive content associated with, for example, an advertising campaign or a specific website. Color choice also influences a consumer's feelings or perception about certain products and/or services, and it plays a role in increased (or decreased) sales generation and/or website traffic. For example, the use of certain colors in an advertising campaign can convey attributes and/or moods an advertiser would like consumers to associate with its products. Further, colors can also be used to capture a user's attention, target specific users, and/or showcase specific product characteristics.

The message and/or intent behind a specific color or color combination choice can be impacted for consumers and/or users affected by vision impairments. Color Vision Deficiency (CVD), sometimes called color blindness, represents a group of vision conditions that affect a person's perception of color. More specifically, CVD is the reduced ability (and in some cases the complete inability) for a person to distinguish between certain hues of color (e.g., between red and green, between blue and yellow, etc.). Common types of CVD include protan (missing and/or malfunctioning L-cones; red), deutan (missing and/or malfunctioning M-cones; green), and tritan (missing and/or malfunctioning S-cones; blue).

Individuals affected by visual impairments such as color vision deficiencies often do not experience content (e.g., online marketing, an advertising campaign, website design, etc.) in the same way as their non-visually-impaired counterparts. For example, as CVD affects around 8% of the population, this means, that for every one hundred users that visits a website or interacts with an application, up to eight users affected by a visual impairment may experience the content of the website much differently than users with normal vision. More specifically, color pairings such as green/red, green/blue, green/gray, green/brown, blue/purple, orange/red, and yellow/orange may be hard to distinguish for a person with deutan CVD. Similarly, those with protan and tritan CVD each have additional unique pairings of problematic color combinations that although distinguishable to those with normal vision, may be difficult (and in some cases impossible) to distinguish for those with a CVD.

To accommodate for color vision impairments and ensure the intent and/or message behind a marketing campaign, data visualization dashboard, or website design can be universally perceived (digitally and/or in print), content creators (e.g., advertisers, marketers, graphic designers, website designers, data analysts, etc.) often design marketing materials, construct websites, generate infographics, and create promotional campaigns with color accessibility in mind. Color accessibility is the practice of choosing colors that enable people with visual impairments or color vision deficiencies to interact with and perceive digital (as well as non-digital) experiences in a similar manner as their non-visually-impaired counterparts. For example, rather than using green and orange (a color pairing that is generally inaccessible for those with deutan and protan CVD) to represent and/or convey certain information on an advertisement, a content creator may select the color pairing of red and blue instead. Oftentimes, however, implementing color accessibility during creation and/or generation has proved challenging.

In an effort to support the implementation of color accessibility when generating content, one conventional approach is the use of color vision simulators. Color vision simulators use manipulation algorithms to simulate the effects of vision defects. For example, a content creator may design a webpage for a website highlighting a winter snow gear sale for consumers. The webpage may use different colors to differentiate between various sale percentage ranges (e.g., 10% off, 30% off, BOGO, clearance, etc.) and/or to categorize the types of gear that are on sale (e.g., helmets, skies, poles, jackets, etc.). Here, after creating the webpage, the content creator can use a color vision simulator to determine how individuals affected by a CVD will perceive the content on the webpage. While color vision simulators provide some level of usefulness in designing color accessible content, they have their limitations.

One such limitation, for example, is that color vision simulators can only be applied to demonstrate the effects of one CVD (e.g., protan, deutan, tritan) at a time, and at a single severity level. Such limitation is problematic because colors chosen for use in marketing materials or webpage design may be accessible for users affected by one type of CVD, but may be inaccessible for users affected by other CVDs. Manually switching between various CVD simulations is not only time consuming and labor intensive, but limits a content creator's ability to determine which color choices best convey the original intent of the webpage design while also being accessible to the most people.

Additionally, color vision simulators are unable to provide real-time feedback on how colors will look to the visually impaired when choosing the colors, because color vision simulators can only be implemented after color choices have been applied to content. In operation, a content creator would need to first generate content and afterwards run a color vision simulator to determine if inaccessibility exists. Here, while the color vision simulator can identify problematic color choices over a range of CVDs (one CVD at a time), a content creator would not know a color choice was inaccessible until after the simulation was run. Correcting for color inaccessibility after content has been created rather than identifying and correcting for color inaccessibility before (or during) content creation negatively impacts design workflow, increases labor costs, and negatively impacts the overall accessibility of generated content. Cost and time inefficiencies increase as the number of colors used increases.

Similarly, color vision simulators do not provide feedback or guidance on how to correct for identified inaccessible color choices. While identifying color inaccessibility is important, such identification is of little use if a content creator is unable to make the necessary corrections. This is particularly significant with novice content creators who might lack the knowledge and understanding of the impact that CVDs have on color perception. Correcting for color inaccessibility through trial and error due to lack of corrective feedback can further have a negative impact on design workflow, an increase labor costs, and a negative impact on the overall accessibility of generated content.

In addition to color vision simulators, other techniques exist for optimizing color accessibility. However, like color vision simulators, these techniques also suffer from limitations. For example, such limitations include their inability to help preserve original design intent (e.g., use of warm tones, earth tones, etc.), their inability for a content creator to supply constraints (e.g., brand constraints, marketing rules, etc.), and their lack of an approachable, user-friendly interface with which to interact, manipulate, and update color choices. Such limitations further impair a content creator's ability to efficiently and adequately identify accessible colors to use during content creation, and can have a severe impact on design workflow, an increase in labor costs, and a negative impact on the overall accessibility of generated content.

Accordingly, techniques described herein are directed to addressing these technical challenges by enabling the optimization of color accessibility during, for example, content creation. In this regard, embodiments described herein leverage the concept of confusion lines to identify and highlight relationships between colors that may be indistinguishable (e.g., inaccessible) for a person with a vision impairment, such as a CVD.

As used herein, confusion lines (e.g., lines of confusion) refer to lines in a color space that represent color confusion for a specific type of CVD. Colors that fall along a confusion line for a given CVD may look the same to a person with that specific type of CVD. For example, if two colors fall along the same protan confusion line, a person with a protan CVD may not be able to distinguish between the two colors (e.g., the distinction between the two colors are not accessible to those with the protan CVD). Further, as used herein, a color space is a representation (e.g., model, organization) of colors and how they are mathematically mapped (or organized) in relationship to each other (e.g., in 3D, 2D, etc.). Some color spaces contain more or less colors depending on the definition of the color space (e.g., HSL, HSV, HSB, Lab, LCh, Luv, CIECAM, etc.). For example, the CMYK color space is a collection of colors that may be printed, and the RGB color space is a collection of colors that may be shown on the display of a user device. Further still, as used herein, a color wheel is a graphical element (e.g., graphical user interface) that may be associated one of a number of different color spaces.

In one embodiment, a graphical user interface, such as a color wheel associated with a color picker, is provided that, by leveraging confusion lines, visually indicates curves of confusion for a color in a color wheel. The curves of confusion for the color in the color wheel may be associated with different types of vision impairments, such as a protan, deutan, and/or tritan CVD. As used herein, curves of confusion generally relate to lines of confusion (or samples and/or points of the lines of confusion) that have been transformed (e.g., by a color transformation, which can be linear or non-linear) from a reference color space to their color equivalent in a color wheel that may be associated with a color picker and/or any number of color spaces. Curves of confusion generally comprise a set of points where, each point on the curve of confusion is in a color conflict (e.g., is indistinguishable) from other colors along that curve of confusion.

In operation, curves of confusion for a selected first color in a color wheel are generated based on receiving a selection of a first location within the color wheel that corresponds to a first color within the color wheel. The color wheel may be associated with a color picker, and may further be displayed on a graphical user interface of a user device. The color wheel may further be associated with any number of color spaces, such as, for example, an HSV, HSL, HSB, Lab, LCh, Luv, HCL, or CIECAM color space. Based on receiving the selection of the first location that corresponds to the first color within the displayed color wheel, the first color within the displayed color wheel may be transformed into its color equivalent in a reference color space. The reference color space may be any number of color spaces, such as a CIE xyY color space (or any other color space where, for example, confusion lines are straight). Transforming the first color into its color equivalent in the reference color space may be based on applying a color transformation to chromaticity coordinates (e.g., color coordinates) associated with the first color in the displayed color wheel.

Based on the first color being transformed into its color equivalent in the reference color space, a first set of colors including the first color in the reference is mapped to a first line of confusion associated with a first type of vision impairment. The first set of colors may be transformed into their color equivalent in the color wheel. The first set of colors may be displayed in the color wheel, where the display of the first set of colors within the color wheel includes a first curve (e.g., a first curve of confusion). The first curve may include a plurality of samples (e.g., points) within the color wheel, where each sample of the plurality of points on the first curve corresponds to one or more colors within the first set of colors. The first curve visually indicates a confusion of colors in the first vision impairment.

By way of non-limiting example, assume a user (e.g., a content creator) selects the color blue on a color wheel, where the color wheel is associated with a color picker. In such an example, after selecting the color blue, a curve of confusion may appear on the color wheel (as described herein in conjunction with FIGS. 1 through 5), where the curve of confusion displayed on the color wheel is associated with a particular CVD (e.g., protan) for the selected blue color, and the curve of confusion visually indicates if a conflict exists with a second selected color for that particular CVD. Here, to generate the protan curve of confusion for the selected blue color, the selected blue color is transformed to its color equivalent in a reference color space, such as a CIE xyY color space, that is associated with the protan CVD. Transforming the selected blue color into its color equivalent in the reference color space is based at least in part on applying a color transformation to the chromaticity coordinates of the selected blue color in the color wheel.

Once the selected blue color is transformed into its color equivalent in the reference color space, a first set of colors that includes the selected blue color is determined (e.g., a protan confusion line associated with the selected blue color is determined). A color transformation is applied to the determined set of colors (e.g., points, samples, etc.) that represents the protan confusion line for the selected blue color in the CIE xyY color space to be displayed on the color wheel as a curve of confusion associated with a protan CVD for the selected blue color. As described herein, when the user (e.g., content creator) repositions the selected blue color on the color wheel (e.g., repositions it to be a lighter or darker blue, repositions it to be a green color, etc.), the curve of confusion associated with the protan CVD iteratively updates and is visually indicated on the color wheel.

In some embodiments, a second and third set of colors each including the first color may be determined, where the second set of colors is mapped to a second line of confusion in the reference color space that is associated with a second type of vision impairment and the third set of colors is mapped to a third line of confusion in the reference color space that is associated with a third type of vision impairment. Based on determining each of the second set and third set of colors, each of the second set and third set of colors may be displayed within the color wheel. Display of the second set of colors includes a second curve within the color wheel that visually indicates a confusion of colors in the second vision impairment. Display of the third set of colors includes a third curve within the color wheel that visually indicates a confusion of colors in the third color vision impairment.

Continuing with our non-limiting example from above, additional curves of confusion (e.g., a second curve and a third curve) may also be determined and displayed on a color wheel for the selected color blue. Here, additional curves of confusion may be determined in a similar way as described above by transforming the selected blue color into its color equivalent in a reference color space, such as a CIE xyY color space, that is associated with the other CVDs, such as deutan CVD and tritan CVD. The additional curves of confusion may be displayed on the color wheel and may indicate whether a conflict exits between the selected blue color and a second selected color for a deutan CVD or a tritan CVD.

In further embodiments, and in response to receiving an input to reposition the first color in the first location to an alternative location corresponding to an alternative color within the color wheel, the first curve may iteratively update to visually indicate an updated confusion of colors in the first vision impairment. Here, updating the first curve is based at least on determining an alternative set of colors that includes the alternative color, where the alternative set of colors is mapped to an alternative line of confusion in the reference color space associated with the first type of vision impairment.

In some embodiments, a selection of a second location within the displayed color wheel may be received. The second location may correspond to a second color within the color wheel. In response to the selection of the second color, a fourth, fifth, and sixth set of colors each associated with a fourth, fifth, and sixth curve within the displayed color wheel may be displayed in the color wheel. Here, display of the fourth curve corresponds to one or more colors within a fourth set of colors, where the fourth curve visually indicates a confusion of colors in the first vision impairment. Similarly, display of the fifth curve corresponds to one or more colors within a fifth set of colors, where the fifth curve visually indicates a confusion of colors in the second vision impairment. Similarly still, display of the sixth curve corresponds to one or more colors within a sixth set of colors, where the sixth curve visually indicates a confusion of colors in the third vision impairment.

Continuing with our non-limiting example from above, assume the user (e.g., the content creator) selects a second color (e.g., yellow) on the color wheel. After selecting the color yellow, curves of confusion may appear on the color wheel (as described herein in conjunction with FIGS. 1 through 5, and as described above), where the curves of confusion displayed on the color wheel are associated with particular CVDs (e.g., protan, deutan, tritan) for the selected yellow color, and the curves of confusion visually indicate if a conflict exists with another selected color for that particular CVD.

In further embodiments, a first curve (e.g., a first curve of confusion) associated with a first color in a first location within a displayed color wheel intersecting a second color in the displayed color wheel visually indicates a confusion of colors (e.g., the colors are indistinguishable) between the first color and the second color for a vision impairment associated with the first curve.

Continuing with our non-limiting example from above, assume that after the user (e.g., the content creator) selects both blue and yellow, that the tritan confusion curve for the blue color intersects the yellow color. In such a case, the intersection of the blue color's tritan curve of confusion with the selected yellow color visually indicates that a conflict exists between the blue color and the yellow color for an individual with a tritan CVD (e.g. the blue and yellow colors are not distinguishable for an individual with a tritan CVD).

In some embodiments, in response to receiving a first color and a second color, it may be determined that both colors are on the same curve of confusion, meaning they are likely indistinguishable from each other. In such an embodiment, there exists a conflict between the first and second colors. In response to determining a conflict exists, an indication within the color wheel may be displayed, where the indication visually indicates the existence of the conflict between the two colors.

In another embodiment, a graphical user interface is provided that, by leveraging confusion lines in an objective function, automatically optimizes a set of input colors for color accessibility. As used herein, an objective function generally refers to a numerical method for optimizing a numerical value. More specifically, an objective function indicates how much each variable (e.g., term) in a set of variables contributes to the numerical value to be optimized (e.g., decreased/minimize, increased/maximized, etc.). Coefficients of an objective function indicate the contribution to the value of the objective function of a corresponding variable. For example, and as described herein, evaluating an objective function on a set of input colors may be based at least on one of a CVD alignment term (e.g., a variable) having a specific weight (e.g., coefficient), an out-of-gamut term (e.g., a variable) having a specific weight (e.g., coefficient), a distinguishability term (e.g., a variable) having a specific weight (e.g., coefficient), and a faithfulness term (e.g., a variable) having a specific weight (e.g., coefficient).

In operation, a set of input colors is automatically optimized for accessibility based on utilizing confusion lines and evaluating an objective function on a selection of a set of input colors. The set of input colors may include a subset of colors that comprises a plurality of updateable colors. The set of input colors may also include a subset of colors that comprises a plurality of static colors that may correspond to receive color constraints. The set of input colors may be selected from within a color wheel on a graphical user interface. The color wheel may be associated with a color picker, and may further be associated with any number of color spaces as described herein. As can be appreciated, however, the set of input colors may be received from somewhere other than a color picker (e.g., a list stored in a data store, etc.).

Based on receiving the set of input colors, each color in the set of colors may be mapped from the color wheel (or from another graphical user interface associated with a color space) to a reference color space, where the mapping is based on applying a color transformation to the set of input colors. Each color in the set of input colors may include a first, second, and third confusion line, where for each color in the set of input colors, the first confusion line is associated with a first type of vision impairment, the second confusion line is associated with a second type of vision impairment, and the third confusion line is associated with a third type of vision impairment. A value may be generated for the set of input colors based on utilizing an objective function that is evaluated on the set of input colors. The objective function may be evaluated using an optimization numerical method, such as, for example, a Nelder-Mead simplex direct search numerical method optimizer. The generated value indicates an accessibility of the set of input colors. The objective function may include at least one of a CVD alignment term, an out-of-gamut term, a distinguishability term, and a faithfulness term. In other words, the objective function computes an accessibility penalty value, and the automatic optimization minimizes the accessibility penalty value, such that the lower the accessibility penalty value, the better (e.g., higher) the accessibility of the set of colors).

The CVD alignment term may indicate conflicts (e.g., an alignment) between colors in the set of input colors. The out-of-gamut term may indicate a location for each color in the set of input colors within the reference color space. Locations outside of a valid range affect (e.g., impact) the final reproduction of the colors in digital and/or physical, and thus should (and in some embodiments must) be avoided. The distinguishability term may indicate a perceptual color difference between colors for each color in the set of input colors. The faithfulness term may indicate the distance between each color in the set of input colors including the plurality of updateable colors and each color of the set of input colors including an updated plurality of updatable colors.

The plurality of updateable colors may be iteratively updated to decrease the value that indicates the accessibility of the set of input colors. Decreasing the value increases the accessibility (e.g., distinguishability) of the set of input colors for a viewer with a CVD. The set of input colors including the updated plurality of updateable colors may then be displayed on a graphical user interface, such as a graphical user interface of a user device. In some embodiments, the set of input colors including the updated plurality of updateable colors may then be displayed on a graphical user interface for further modification (e.g., manual updating, color changes, color adjustments, etc.).

Advantageously, technologies described by the current disclosure reduce the cost and time inefficiencies associated with color accessible content creation, as well as improve the overall workflow associated with creating color accessible content. In providing a graphical user interface that displays curves of confusion associated with selected colors that update as a color selection is manipulated (e.g., the color associated with the selection is repositioned on a color wheel), the disclosed technologies leverage confusion lines to provide a user-friendly interface for providing real-time color accessibility and color confusion feedback. The inventive operations disclosed herein further result in efficiency in user navigation of graphical user interfaces (e.g., such as a color wheel associated with a color picker), and identification of accessible colors (e.g., such as during content creation). The real-time (or near real-time) feedback visually displayed on a graphical user interface may also include indications of color conflicts between colors for various types of vision impairments (e.g., protan, deutan, and tritan CVD), simultaneously. Moreover, in enabling the automatic optimization of color accessibility for a set of input colors, the disclosed technologies further leverage confusion lines to provide a labor- and cost-efficient, real-time technique for generating accessible color themes.

In this regard, the accessible color optimization operations described herein facilitate determining color accessible colors, while providing visual indications that indicate (e.g., provide awareness) when color conflicts exist so that a user (e.g., a content creator) may make appropriate modifications. Moreover, the accessible color optimization operations facilitate the automatic generation of accessible colors, while taking into consideration color constraints input by a user (e.g., content creator), as well as maintaining the original color theme present in the set of input colors.

Turning now to FIG. 1, a schematic depiction is provided illustrating an exemplary accessible color optimization environment 100 in which some embodiments of the present disclosure may be employed. Among other components not shown, accessible color optimization environment 100 may include an accessible color optimization engine 102, a user device, such as user devices 104A, 104B, and 104C, a data store 106, and a distributed computing environment 110. Distributed computer environment 110 hosts accessible color optimization engine 102. It should be understood that accessible color optimization environment 100 shown in FIG. 1 is an example of one suitable computing system. Any of the components shown in FIG. 1 is an example of one suitable computing system. Any of the components shown in FIG. 1 may be implemented via any type of computing device, such as computing device 1300 described with reference to FIG. 13, for example. The components may communicate with each other via one or more networks 108, which may include, without limitation, one or more local area networks (LANs) and/or wide area networks (WANs). Such networking environments are commonplace in offices, enterprise-wide computer networks, intranets, and the Internet.

It should be understood that this and other arrangements described herein are set forth only as examples. Other arrangements and elements (e.g., machines, interfaces, functions, orders, groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Generally, accessible color optimization environment 100 facilitates color accessibility optimization by leveraging lines of confusion to identify and highlight relationships between colors that may be inaccessible (e.g., undistinguishable) for a person with a vision impairment, such as a color vision deficiency. In one embodiment, and at a high-level, a graphical user interface is provided that visually indicates curves of confusion for each of the colors in the selection. Each curve of confusion visually indicates a confusion of colors for a type of vision impairment, such as a CVD. As a color from the selection of colors is repositioned within the color wheel, the curves of confusion associated with that color are iteratively updated. In embodiments, when a curve of confusion associated with a first color intersects a second color, the intersection visually indicates a confusion of colors between the first color and the second color for the type of vision impairment for that curve of confusion. When a color selection within the color wheel is changed (e.g., repositioned), the curves of confusion update to visually indicate curves of confusion associated with the repositioned color.

In operation, a selection of a first color from a color wheel associated with a color picker displayed on a graphical user interface is received at an accessible color optimization engine, such as accessible color optimization engine 102 of FIG. 1. Based on receiving the selection of the first color within the displayed color wheel, the first color may be transformed into its color equivalent in a color space different from the displayed color wheel. The color space may be any number of color spaces where confusion lines are straight, such as a CIE xyY color space. Transforming the first color into its color equivalent may be based on applying a color transformation to chromaticity coordinates (e.g., color coordinates) associated with the first color in the displayed color wheel. Based on receiving the selection of the first color, and subsequent to transforming the first color into its color equivalent, a first set of colors is determined that includes the first color. Here, the determined first set of colors is mapped to a first line of confusion in the color space that is associated with a first type of vision impairment. Once determined, the first set of colors may be transformed into their color equivalent within the color wheel and be displayed in the color wheel as a first curve (e.g., a curve of confusion). The first curve may include a plurality of points within the color wheel, where each point of the plurality of points on the first curve corresponds to one or more colors within the first set of colors. Here, the first curve visually indicates a confusion of colors associated with the first vision impairment.

By way of non-limiting example, assume a user (e.g., a webpage designer) desires to create a webpage for selling tickets for a concert at a concert venue. Assume the webpage designer desires to use different colors to denote seating availability (e.g., differentiate between available and unavailable seats). Assume further that the webpage designer desires to use different colors to denote seat availability for various pre-sale categories (e.g., VIP pre-sale, Insider pre-sale, Fan group pre-sale, etc.). In designing the webpage, the webpage designer desires that viewers with a vision impairment, such as a CVD, be able to view and interact with the content of the webpage in a similar manner to viewers without visual impairment. In such a case, the webpage designer may select a set of colors associated with a color wheel, such as a color wheel associated with a color picker) which the webpage designer desires to use to denote seating availability and pre-sale category. For each color selected on the color wheel, curves of confusion associated with each selected color may be displayed, where each curve of confusion visually indicates a confusion of colors for a type of vision impairment, such as a CVD.

A color conflict for a particular vision impairment exists when a curve of confusion associated with the particular vision impairment for one color intersects the location of a second color on the color wheel. In such a case where a color conflict exists, the webpage designer may reposition one of the colors in conflict to eliminate the conflict. As a color is repositioned on the color wheel, the curves of confusion associated with that color iteratively update to visually indicate updated confusions of colors. In this regard, an accessible color optimization engine, such as accessible color optimization engine 102 of FIG. 1 determines and displays curves of confusion associated with the selected colors. The webpage designer may reposition the colors until the colors are accessible for viewers with a vision impairment (e.g., until no conflicts of color exist), such as a CVD. Using the now accessible colors, the webpage designer can create the concert venue webpage knowing the colors selected will be accessible to viewers of the webpage both with and without a CVD.

In other embodiments, confusion lines may be utilized to automatically generate a set of colors that are accessible to those with vision impairments, such as a CVD. In operation, a selection of a set of input colors is received at an accessible color optimization engine, such as accessible color optimization engine 102 of FIG. 1. The set of input colors may be selected from a color space (e.g., a color wheel). The set of input colors may include a set of color constraints (e.g., static colors) as well as colors that may be updated. The color constraints may be associated with guidelines, such as, for example, brand-specific guidelines and/or marketing campaign themes.

The set of input colors may be optimized by utilizing an objective function. When evaluated on the set of input colors using, for example, an optimizer (e.g., a Nelder-Mead simplex direct search numerical method optimizer), the objective function may determine a value indicating the accessibility of the set of colors. Evaluating the objective function on the set of input colors may be based on determining at least one of a CVD alignment term, an out-of-gamut term, a distinguishability term, and a faithfulness term for the set of colors. As the value decreases, the accessibility of the set of input colors also increases. Once determined, an updated (e.g., accessible) set of colors may be displayed, such as on a graphical user interface of a user device. In some embodiments, the updated set of colors may be displayed for further modification, such as, for example, by a user (e.g., content creator).

By way of non-limiting example, assume a user (e.g., a marketing associate) desires to create an advertisement for selling tax software. Assume the marketing associate desires to use different colors to differentiate the pros and cons between the marketing associate's tax software and competitor's tax software. Assume further that the marketing associate also desires that at least one of the colors used in creating the advertisement aligns with the brand constraints of the marketing associate's employer. In designing the advertisement, the marketing associate desires that viewers with a vision impairment, such as a CVD, be able to view the content of the advertisement in a similar manner to viewers without visual impairment. In such a case, the marketing associate may select a set of colors associated with a color wheel, such as a color wheel associated with a color picker. The marketing associate may also select color constraints (e.g., static colors) that will remain the same during color accessibility optimization. Using confusion lines and an objective function, the set of colors may be optimized for accessibility. After optimization, an updated set of colors that is accessible to viewers of the advertisement, including the color associated with the color constraint may be displayed on a graphical user interface. In some cases, the updated set of colors including the color associated with the color constraint may be displayed to the marketing associate on a graphical user interface for further modification.

Returning to FIG. 1, in operation, a user device, such as user devices 104A through 104C, can access accessible color optimization engine 102, hosted by the distributed computing environment 110 (e.g., a server), over a network 108 (e.g., a LAN or the Internet). For instance, a user device, such as user devices 104A through 104C may provide and/or receive data from the accessible color optimization engine 102 via the network 108. Network 108 may include multiple networks, or a network of networks, but is shown in a simple form so that not to obscure of the present disclosure. By way of example non-limiting, network 108 can include one or more wide area networks (WANs), one or more local area networks (LANs), one or more public networks, such as the Internet, and/or one or more private networks. Networking environments are commonplace in offices, enterprise-wide computer networks, intranets, and the Internet. Accordingly, network 108 is not described in significant detail.

A user device, such as user devices 104A through 104C, may be any computing device that is capable of facilitating a user (e.g., content creator, designer, marketer, advertiser, etc.) to select a color or set of colors from a color wheel associated with a color picker.

In some embodiments, in response to providing a selection of a color or set of colors, a user device, such as user devices 104A through 104C, may display curves of confusion associated with each color selected within the color wheel. In other embodiments, in response to providing a selection of a color or set of colors, a user device, such as user devices 104A through 104C, may display an updated color or set of colors that is accessible (e.g., distinguishable) to those with a vision impairment, such as, for example, a CVD.

In some cases, a user device, such as user devices 104A through 104C, accesses the accessible color optimization engine 102 via a web browser, terminal, or standalone PC application operable on the user device. A user device, such as user devices 104A through 104C, may be operated by an administrator, which may be an individual or set of individuals that manages color accessibility optimization for use in content creation, for example. For instance, a user (e.g. content creator) may be any individual, such as a designer, advertiser, marketer, promoter, and/or website designer associated with an entity (e.g., an organization) that desires to optimize a color or set of colors for use in generating content. (e.g., designing a webpage, creating an advertisement, etc.).

While only user devices 104A through 104C are illustrated in FIG. 1, multiple other user devices associated with any number of users may be utilized to carry out embodiments described herein. A user device, such as user devices 104A through 104C, may take on a variety of forms, such as a personal computer (PC), a laptop computer, a mobile phone, a tablet computer, a wearable computer, a personal digital assistant (PDA), an MP3 player, a global positioning system (GPS) device, a video player, a digital video recorder (DVR), a cable box, a set-top box, a handheld communications device, a smart phone, a smart watch, a workstation, any combination of these delineated devices, or any other suitable device. Further, a user device, such as user devices 104A through 104C, may include one or more processors, and one or more computer-readable media. The computer-readable media may include computer-readable instructions executable by the one or more processors.

In some cases, a user of distributed computing environment 110 may employ one or more user interfaces via a web browser, terminal, or standalone PC application operable on the distributed computing environment to control and/or operate dynamic content generation engine 102 to generate candidate image units. Users of distributed computing environment 110 may further control and/or operate accessible color optimization engine 102 to optimize the accessibility of colors that may be displayed on a user device, such as user devices 104A through 104C. Distributed computing environment 110 may be operated by an administrator, which may be an individual or set of individuals that manages color accessibility optimization for use in content creation, for example. For instance, a user (e.g. content creator) may be any individual, such as a designer, advertiser, marketer, promoter, and/or website designer associated with an entity (e.g., an organization) that desires to optimize a color or set of colors for use in generating content. (e.g., designing a webpage, creating an advertisement, etc.). While only distributed computing environment 110 is illustrated in FIG. 1, multiple other distributed computing devices associated with any number of users may be utilized to carry out embodiments described herein.

A distributed computing environment, such as distributed computing environment 110, may take on a variety of forms such as a server, personal computer (PC), a laptop computer, a mobile phone, a tablet computer, a wearable computer, a personal digital assistant (PDA), an MP3 player, a global positioning system (GPS) device, a video player, a digital video recorder (DVR), a cable box, a set-top box, a handheld communications device, a smart phone, a smart watch, a workstation, any combination of these delineated devices, or any other suitable device. Further, a distributed computing environment, such as distributed computing environment 110, may include one or more processors, and one or more computer-readable media. The computer-readable media may include computer-readable instructions executable by the one or more processors.

The data store 106 includes, among other data, color data that may contain desired information used to optimize color accessibility. As described in more detail below, the data store 106 may include color data including chromaticity coordinates (e.g., color coordinates) of colors associated with various color spaces, such as CIE xyY, RGB, sRGB, HSV, HSL, CMYK, etc. color spaces and metadata associated therewith. Data store 106 may also include color transformation data relating to transforming a color in a color wheel to its color equivalent in a reference color space. Data store 106 may also include confusion line data associated with various color spaces and metadata associated therewith. Such data may be stored in the data store 106 and accessible to any component of the accessible color optimization environment 100. Data store 106 may also be updated at any time, including an increase or decrease in the amount of color data, color space data, or color transformation data stored therein. Further, the color data, and/or any other data, contained within data store 106 may be changed, altered, updated, or the like, at any time.

The accessible color optimization engine 102 is generally configured to optimize for color accessibility during, for example, content creation. As described herein, in one embodiment, a graphical user interface is provided that, by leveraging confusion lines, visually indicates curves of confusion for a color in a color space, such as a color wheel associated with a color picker. In particular, accessible color optimization engine 102 can receive a selection of a first color in a color wheel with a corresponding location, determine a set of colors including the first color, where the set of colors is mapped to a first line of confusion associated with a first type of vision impairment, and display the first set of colors in the color wheel where the display includes a first curve of confusion where the first curve of confusion visually indicates a confusion of colors in the first type of vision impairment.

As further described herein, in another embodiment a graphical user interface is provided that, by leveraging confusion lines and an objective function, automatically optimizes a set of input colors for color accessibility. In particular, accessible color optimization engine 102 can receive a selection of a set of input of colors that includes a subset of colors that comprises a plurality of updatable colors. A value that indicates an accessibility of the set of colors is determined by evaluating the objective function on the set of input colors. The set of input colors is iteratively updated to decrease the value that indicates the accessibility of the set of input colors. The set of input colors, including the updated plurality of updatable colors may be displayed in a graphical user interface. In some embodiments, the set of input colors, including the updated plurality of updatable colors may be displayed in a graphical user interface for further modification, such as manual modification by a user (e.g., content creator).

Although FIG. 1 illustrates a distributed system in which accessible color optimization engine 102 is located on a server remote from user devices 104A through 104C e.g., distributed computing environment 110), in other embodiments, accessible color optimization engine 102 can be located on, executed by, or otherwise installed on a user device, such as user devices 104A through 104C. Additionally and/or alternatively, in other embodiments, at least one component of accessible color optimization engine 102 can be located on a user device, such as user devices 104A through 104C.

Figure 2:
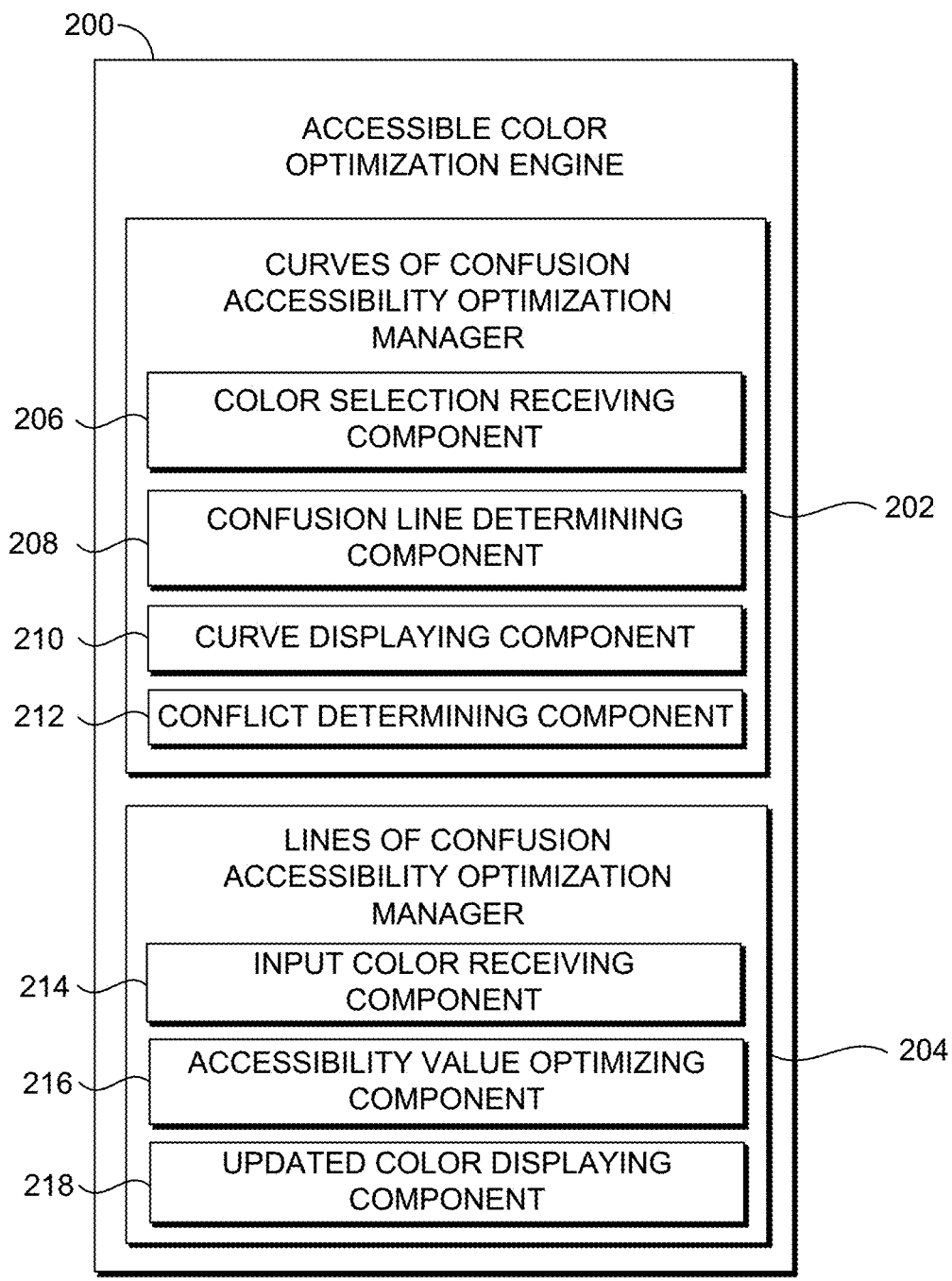
FIG. 2 is a depiction of an accessible color optimization engine, in accordance with embodiments of the present disclosure.

An exemplary accessible color optimization engine is provided in FIG. 2. As shown in FIG. 2, accessible color optimization engine 200 includes curves of confusion accessibility optimization manager 202 and lines of confusion accessibility optimization manager 204. Curves of confusion accessibility optimization manager 202 is generally configured to generate and visually indicate curves of confusion for a color in a color space, such as a color wheel associated with a color picker, using lines of confusion. Lines of confusion accessibility optimization manager 204 is generally configured to automatically optimize a set of input colors for color accessibility using lines of confusion and an objective function.

Although illustrated as separate components of accessible color optimization engine 200, any number of components can be used to perform the functionality described herein. Further, although illustrated as being a part of an accessible color optimization engine, the components can be distributed via any number of devices. For example, curves of confusion accessibility optimization manager 202 can be provided via one device (e.g., a user device, such as user devices 104A through 104C of FIG. 1), server, or cluster of servers, while lines of confusion accessibility optimization manger 204 can be provided via another device, server, or cluster of servers. The components identified herein are merely set out as examples to simplify or clarify the discussion of functionality. Other arrangements and elements (e.g., machine, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more components may be carried out by hardware, firmware, and/or software. For instance, various functions may be carried out by a processor executing instructions stored in memory.

As described, curves of confusion accessibility optimization manger 202 generally is configured to generate and visually indicate curves of confusion for a color in a color space, such as a color wheel associated with a color picker, using lines of confusion. As illustrated, curves of confusion accessibility optimization manger 202 includes color selection receiving component 206, confusion line determining component 208, curve displaying component 210, and conflict determining component 212. Although illustrated as separate components of curves of confusion accessibility optimization manger 202, any number of components can be used to perform the functionality described herein.

Color selection receiving component 206 is generally configured to receive a selection of a first location within a color wheel displayed within a graphical user interface. As described, the selection of the first location is associated with a first color within the color wheel. The color wheel can represent a color picker, and may be associated with any number of color spaces, such as an HSV, HSL, HSB, Lab, LCh, Luv, HCL, or CIECAM color space. The first location within the color wheel may further be associated with chromaticity coordinates (e.g., color coordinates). By way of non-limiting example, (108°, 76.9%, 86.7%) is a color coordinate associated with an HSV color space. In some cases, the color selection is provided by a user (e.g., content creator, website designer, marketer, etc.) of accessible color optimization engine 200. As an example, a user might select a color or set of colors via a user device, such as user devices 104A through 104C of FIG. 1, which is connected to the network 108.

Confusion line determining component 208 is generally configured to determine confusion lines associated with each color of the selection of colors received by color selection receiving component 206. As described herein, based on receiving a first color associated with a first location within a color wheel, confusion line determining component 208 transforms the selected first color to its color equivalent a reference color space (e.g., a CIE xyY color space). Transforming the first color into its color equivalent in the reference color space may be based at least on applying a color transformation to chromaticity coordinates (e.g., color coordinates) associated with the first color in the displayed color wheel. As can be appreciated, various transformations exist to transform a color in a color wheel (associated with a color space) into its color equivalent in a reference color space.

Based on confusion line determining component 208 transforming the first color into its color equivalent in the reference color space, confusion line determining component 208 can determine a first set of colors that includes the first color, where the first set of colors is mapped to a first line of confusion associated with a first type of vision impairment. For example, a first line of confusion for the first color may be associated with a protan CVD. In other examples, additional lines of confusion associated with the first color may be associated with other vision impairments, such as deutan CVD and/or tritan CVD.

Curve displaying component 210 is generally configured to display curves of confusion for each selected color in a color wheel, such as a color wheel associated with a color picker. As described herein, based on determining the first set of colors that includes the first color, where the first set of colors is mapped to a first line of confusion associated with a first type of vision impairment, curve displaying component 210 may transform the first set of colors into their color equivalents on the color wheel (e.g., using a color transformation). Curve displaying component 210 may display the transformed first set of colors in the color wheel, where the display of the first set of colors within the color wheel corresponds to a first curve (e.g., a first curve of confusion) associated with the first type of vision impairment. The first curve may include a plurality of points within the color wheel, where each point of the plurality of points on the first curve corresponds to one or more colors within the first set of colors. The first curve visually indicates a confusion of colors in the first vision impairment.

Curve displaying component 210 is further configured to, in response to receiving an input to reposition the first color in the first location to an alternative location corresponding to an alternative color within the color wheel, iteratively update the first curve to visually indicate an updated confusion of colors in the first vision impairment. Here, updating the first curve is based at least on determining an alternative set of colors (e.g., via a confusion line determining component, such as confusion line determining component 208) that includes the alternative color, where the alternative set of colors is mapped to an alternative line of confusion in the reference associated with the first type of vision impairment.

Conflict determining component 212 is generally configured to determine whether a conflict of colors exists, and if so, visually indicate the existence of the conflict on the color wheel. Here, upon determining that a first curve (e.g., a first curve of confusion) associated with a first color in a first location within a displayed color wheel intersects a selected second color in the displayed color wheel, conflict determining component 212 may visually indicate a confusion of colors (e.g., a color conflict) exists between the first color and the second color for a vision impairment associated with the first curve. For example, if a protan curve of confusion associated with a selected color blue intersects with a selected color green on a color wheel, a conflict (e.g., confusion of colors) exists between the blue color and the green color. Here, a confusion of colors indicates that for a viewer with a protan CVD, the blue color and the green color are indistinguishable.

Figure 5:
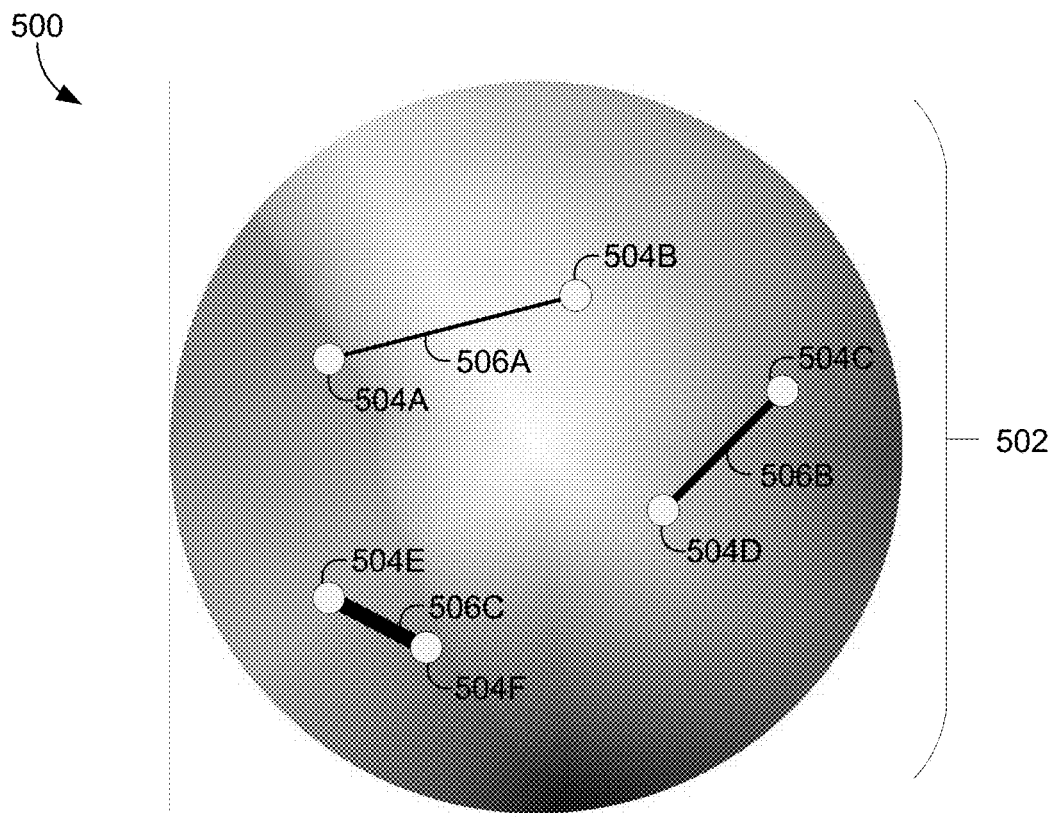
FIG. 5 is a schematic diagram showing an exemplary user interface illustrating conflict lines between colors, in accordance with embodiments of the present disclosure.

Conflict determining component 212 visually indicates a confusion of colors exists by, for example, visually displaying a line between the two colors in conflict on the color wheel, such as color conflict lines 504A, 504B, and 504C of FIG. 5. As can be appreciated, color conflicts exist in varying severities. For example, based on various characteristics (e.g., hue, saturation, contrast) of two colors, a conflict between the two colors may be either more or less severe. Conflict determining component 212 visually indicates a confusion of colors between colors based at least in part on the level of severity of the color conflict. By way of example, conflict determining component 212 may visually indicate different levels of severity my varying the width of the color conflict line between colors.

As described, lines of confusion accessibility optimization manger 204 generally is configured to facilitate automatically optimizing a set of input colors for color accessibility using lines of confusion and an objective function. As illustrated, lines of confusion accessibility optimization manger 204 includes input color receiving component 214, accessibility value optimizing component 216, updated color displaying component 218. Although illustrated as separate components of lines of confusion accessibility optimization manger 204, any number of components can be used to perform the functionality described herein.

Input color receiving component 214 is generally configured to receive a set of input colors that includes a subset of colors that comprises a plurality of updatable colors. The set of input colors may further include color constraints that denote a plurality of static colors (e.g., colors that will not be optimized, for example, due to brand guidelines,). As described herein, the selection of the set of input colors may be associated with various color spaces, such as, for example, an HSV, HSL, HSB, Lab, LCh, Luv, HCL, or CIECAM color space. In some cases, the set of input colors may be provided by a user (e.g., content creator, website designer, marketer, etc.) of accessible color optimization engine 200. As an example, a user might select the set of input colors via a user device, such as user devices 104A through 104C of FIG. 1, which is connected to the network 108. In some embodiments, the user may select the set of input colors using a color wheel associated with a color picker.

Accessibility value optimizing component 216 is generally configured to optimize the set of input colors for color accessibility. Based on receiving the set of input colors (e.g., ordered or unordered), accessibility value optimizing component 216 generates (e.g., determines) a value that indicates an accessibility of the set of colors. To determine the accessibility value, accessibility value optimizing component 216 evaluates an objective function on the set of input colors. The objective function may be evaluated (e.g., optimized) on the set of input colors, using, for example, an optimizer (e.g., a Nelder-Mead simplex direct search numerical method optimizer).

In operation, given a color palette (e.g., set of input colors) with n colors, $P=\{p_1, p_2, \ldots p_n\}$ for $n \geq 2$ P. $P_f$ are colors that may be defined in a color space, such as a CIE xyY color space, where confusion lines remain straight. $P_f$ are the colors associated with color constraints (e.g., static colors that are not to be optimized). $P_o$ are the colors to be optimized (e.g., $P_o = P - P_f$). $L_i$ are the unit vectors for each line of confusion passing through $P_i^*$, with $P_i^*$. $L_i = \{pro_i, deu_i, tri_i\}$ are the unit vectors for confusion lines associated with the various types of CVD (e.g., protan, deutan, and tritan).

The objective function utilized by accessibility value optimizing component 216 and evaluated on the set of colors may be expressed by:

$$e = \sum_{i=1}^{4} w_i * e_i \qquad \text{Equation (1)}$$

where $e_i$ indicates the terms considered by the objective function (e.g., a CVD alignment term, an out-of-gamut term, a distinguishability term, and a faithfulness term), $w_i$ indicates a weight associated with a corresponding term considered by the objective function, and e indicates a determined similarity value for a set of input colors. As described herein, to evaluate the objective function, an optimizer is used, such as, for example, the Nelder-Mead simplex direct search numerical method optimizer. As can be appreciated, other optimizers of similar characteristics may be appropriate for evaluating the objective function described herein.

As described herein, the objective function may include at least one of a CVD alignment term, an out-of-gamut term, a distinguishability term, and a faithfulness term. The CVD alignment term may indicate an alignment between each color in the set of input colors and confusion lines (e.g., how far a first color is from a second color's confusion lines). The CVD alignment term utilized by the objective function and evaluated on the set of input colors may be expressed by:

$$e_1 = \sum_{i \in n} \sum_{j \in n} \sum_{i \in L_j} \left|1 \cdot \overrightarrow{p_i^* p_j^*}\right|^{\tau_1} \quad \text{Equation (2)}$$

where $\overrightarrow{p_i^* p_j^*}$ is the unit vector between colors i (e.g., a first color) and j (e.g., a second color) for the current step of the optimization, and $\tau_1$ is a threshold used to achieve a smooth and quick falloff towards 0 when the angle ($\theta°$) between unit vector $\overrightarrow{p_i^* p_j^*}$ and a confusion line for a color (e.g., $P_i^*$) is greater than zero. In some embodiments, $\tau_1=50$ by default. However, as can be appreciated, $\tau_1$ may be set to other values as well. In some embodiments, a weight for the faithfulness term is $w_1=1$ by default. However, as can be appreciated, $w_1$ may be set to other values as well.

The out-of-gamut term utilized by the objective function and evaluated on the set of input colors is expressed by:

$$e_2 = \sum_{i \in n} \sum_{c \in \{R,G,B\}} \left|\min\left(p_{i,c}^*, 0\right)\right| + \max\left(p_{i,c}^* - 1, 0\right) \quad \text{Equation (3)}$$

where $p_{i,c}^*$ is channel c of $p_i^*$ after converting it to an RGB color space for display. In some embodiments, an sRGB color space is used such that a selection of input colors is transformed from a CIE xyY color space to an sRGB color space. The transformation is performed without clamping so RGB values are not limited to a value range between 0 and 1. When computing $e_2$, the residual amount either below 0 or above 1 may be used as the amount of color out-of-gamut. In some embodiments, a weight for the out-of-gamut term is $w_2=1000$ by default because no color can be out-of-gamut. However, as can be appreciated, $w_2$ may be set to other values as well.

The distinguishability term utilized by the objective function and evaluated on the set of input colors is expressed by:

$$e_3 = \sum_{i \in n} \sum_{j \in n} \frac{1}{\Delta E(p_i^*, p_j^*)^{\tau_2}} \quad \text{Equation (4)}$$

where $\Delta E$ (e.g., dE, Delta-E) is a perceptual color difference between two colors (e.g., the visible difference, or error, between two colors mathematically). In some embodiments, CIE $\Delta E$ 2000 is used. As can be appreciated, however, other $\Delta E$ formulations may be used, such as, for example, CIE76, CIE94, and CMC I:c (1984). $\tau_2$ is a threshold that controls a smooth falloff for this term. In some embodiments, $\tau_2=1$ by default. However, as can be appreciated, $\tau_2$ may be set to other values as well, such as, for example, smaller numbers to achieve more distinguishable (e.g., more accessible) colors. In some embodiments, a weight for the distinguishability term is $w_3=20$ by default. However, as can be appreciated, $w_3$ may be set to other values as well.

The faithfulness term utilized by the objective function and evaluated on the set of input colors is expressed by:

$$e_4 = \sum_{i \in n} \Delta E(p_i^*, p_i) \quad \text{Equation (5)}$$

where similar to Equation (4), $\Delta E$ (e.g., dE, Delta-E) is a perceptual color difference between two colors (e.g., the visible difference, or error, between two colors mathematically). In some embodiments, CIE $\Delta E$ 2000 is used. As can be appreciated, however, other $\Delta E$ formulations may be used, such as, for example, CIE76, CIE94, and CMC I:c (1984). In some embodiments, a weight for the faithfulness term is $w_4=0.001$ by default. However, as can be appreciated, $w_4$ may be set to other values as well.

Utilizing the objective function, accessibility value optimizing component 216 can iteratively update the plurality of updateable colors included in the set of input colors to decrease the value that indicates an accessibility of the set of input colors. Decreasing the accessibility value decreases the accessibility (e.g., increases distinguishability) of the set of input colors.

Updated color displaying component 218 is generally configured to cause display of the set of input colors including the updated plurality of updateable colors on a graphical user interface, such as a graphical user interface of a user device. In some embodiments, updated color displaying component 218 may cause display of the set of input colors including the updated plurality of updateable colors on a graphical user interface for further modification (e.g., manual updating, color changes, color adjustments, etc.).

Figure 3:
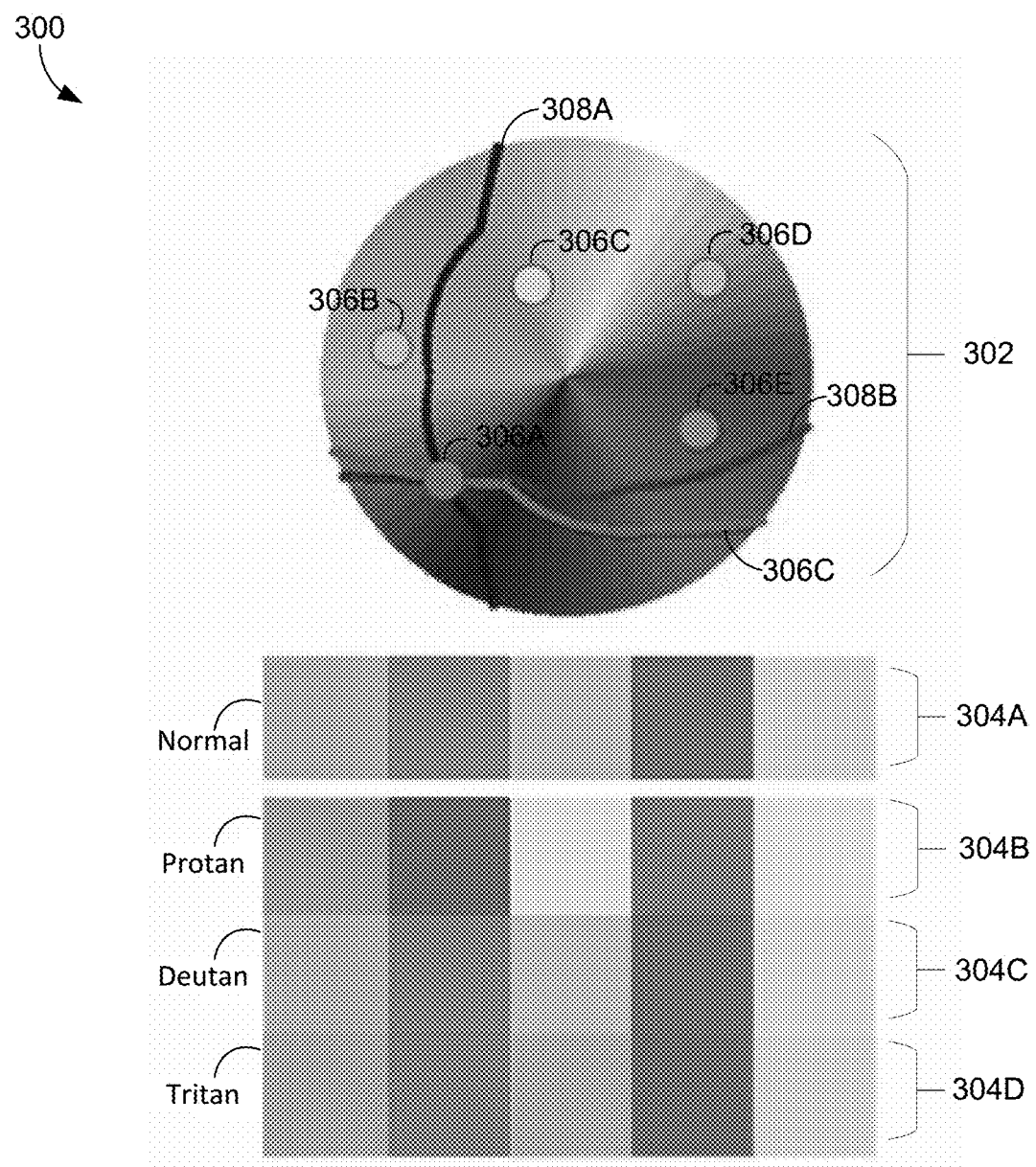
FIG. 3 is a schematic diagram showing an exemplary user interface illustrating curves of confusion associated with colors within a color wheel, in accordance with embodiments of the present disclosure.
Figure 4:
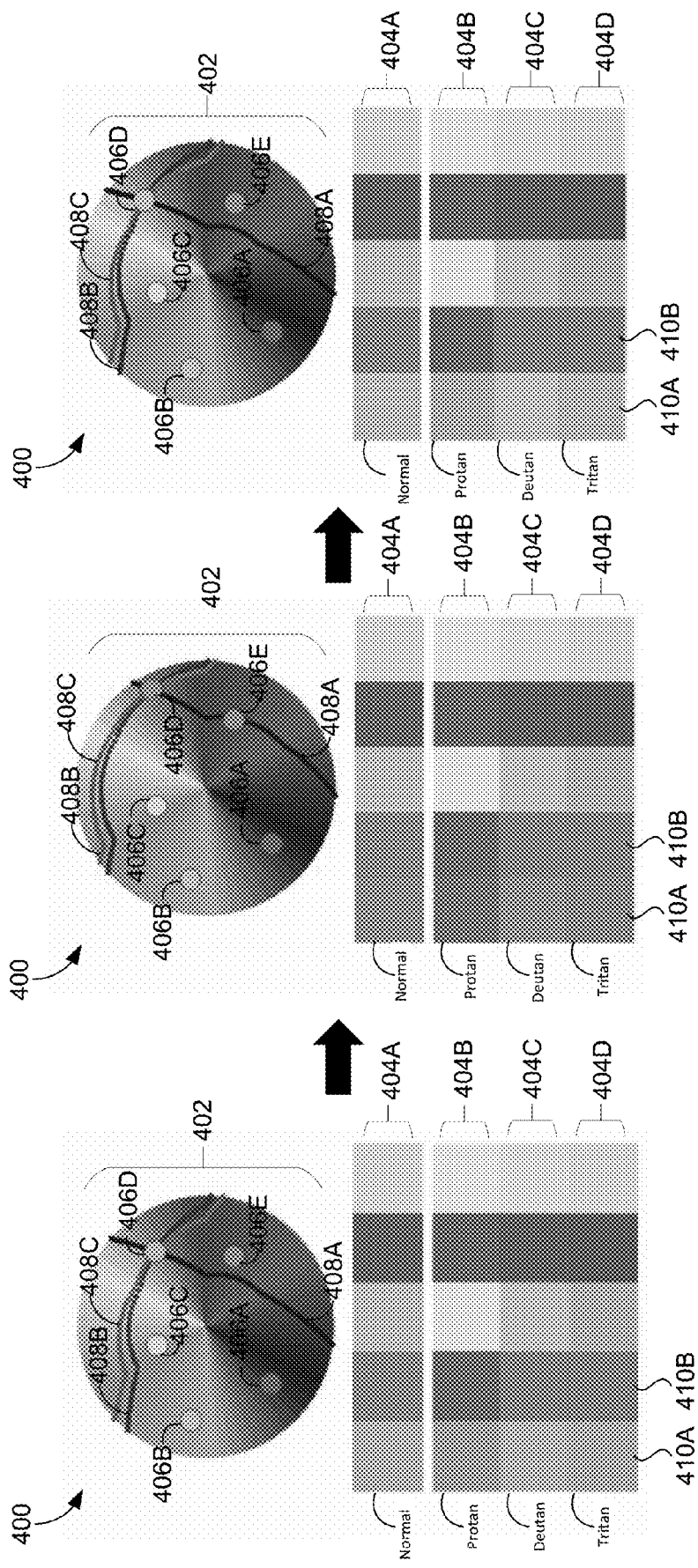
FIGS. 4A-4C are schematic diagrams showing exemplary user interfaces illustrating curves of confusion associated with a color within a color wheel iteratively updating when the color is repositioned, as well as a confusion of colors between two colors within the color wheel, in accordance with embodiments of the present disclosure.

Turing now to FIG. 3, an exemplary user interface is provided illustrating curves of confusion associated with colors within a color wheel, designated generally as user interface 300. The user interface 300 is displayed via a user device, such as user devices 104A through 104C of FIG. 1. The user interface 300 includes color wheel 302, color palettes 304A through 304D, colors 306A through 306E, and confusion curves 308A through 308C. Color wheel 302 maybe associated with a color space, such as, for example, an HSV, HSL, HSB, Lab, LCh, Luv, HCL, or CIECAM color space. Color palette 304A visually indicates how colors 306A through 306E are visually perceived for someone without a vision impairment. Color palette 304B visually indicates how colors 306A through 306E are visually perceived for someone with a protan CVD vision impairment. Color palette 304C visually indicates how colors 306A through 306E are visually perceived for someone with a deutan CVD vision impairment. Color palette 304D visually indicates how colors 306A through 306E are visually perceived for someone with a tritan CVD vision impairment.

Confusion curves 308A through 308C visually indicate confusions of colors associated with color 306A. Specifically, confusion curve 308A visually indicates confusions of colors associated with tritan CVD. Confusion curve 308B visually indicates confusions of colors associated with protan CVD. Confusion curve 308C visually indicates confusions of colors associated with deutan CVD. As described herein, upon receiving an indication to reposition color 306A, confusion curves 308A through 308C would iteratively update (in real-time) to visually indicate confusions of colors associated with color 306A in a repositioned location.

Turing now to FIGS. 4A through 4C, exemplary user interfaces are provided illustrating curves of confusion associated with a color within a color wheel that iteratively updates as a result of the color being repositioned, as well as a confusion of colors between two colors within the color wheel as a result of the repositioning. For each of FIG. 4A though 4C, the user interface is designated generally as user interface 400. User interface 400 is displayed via a user device, such as user devices 104A through 104C of FIG. 1. User interface 400 includes color wheel 402, color palettes 404A through 404D, colors 406A through 406E, and confusion curves 408A through 408C associated with color 406D. Color wheel 402 maybe associated with a color space, such as, for example, an HSV, HSL, HSB, Lab, LCh, Luv, HCL, or CIECAM color space.

In the examples illustrated by FIGS. 4A through 4C, color palette 404A visually indicates how colors 406A through 406E are visually perceived for someone without a vision impairment. Color palette 404B visually indicates how colors 406A through 406E are visually perceived for someone with a protan CVD vision impairment. Color palette 404C visually indicates how colors 406A through 406E are visually perceived for someone with a deutan CVD vision impairment. Color palette 404D visually indicates how colors 406A through 406E are visually perceived for someone with a tritan CVD vision impairment. Color palette 404D includes color 410A that visually indicates how color 406D is visually perceived for someone with a tritan CVD vision impairment. Color palette 404D also includes color 410B that visually indicates how color 406E is visually perceived for someone with a tritan CVD vision impairment. As can be seen in FIG. 4A, color 410A and color 410B are color accessible. Confusion curves 408A through 408C visually indicate confusions of colors associated with color 406D. Specifically, confusion curve 408A visually indicates confusions of colors associated with tritan CVD. Confusion curve 408B visually indicates confusions of colors associated with protan CVD. Confusion curve 408C visually indicates confusions of colors associated with deutan CVD. As can be seen in FIG. 4A, confusion curves 408A through 408C do not intersect any other selected color in color wheel 402 (e.g., there are no color conflicts).

As described herein, upon receiving an indication to reposition color 406D to a different location within color wheel 402, confusion curves 408A through 408C iteratively update (in real-time). FIG. 4B visually indicates the result of repositioning color 406D. Here, FIG. 4B visually indicates confusion curves associated with color 406D in a repositioned location within color wheel 402. Specifically, in response to the repositioning, confusion curve 408A associated with color 406D intersects color 406E. Such intersection visually indicates a confusion of colors between color 406D and color 406E associated with tritan CVD. As a result, color 410A and color 410B in color palette 404D of FIG. 4B are color inaccessible for someone with a tritan CVD vision impairment.

As described herein, upon receiving another indication to reposition color 406D in yet another different location within color wheel 402, confusion curves 408A through 408C again iteratively update (in real-time). FIG. 4C visually indicates the result of repositioning color 406D to a different location from that of its location in FIGS. 4A and 4B. Here, FIG. 4C visually indicates confusion curves associated with color 406D in a second repositioned location within color wheel 402. Specifically, in response to the repositioning of color 406D, confusion curve 408A associated with color 406D no longer intersects color 406E, thus visually indicating that no confusion of colors exists between color 406D and color 406E associated with tritan CVD. As a result, color 410A and color 410B in color palette 404D of FIG. 4C are again color accessible for someone with a tritan CVD vision impairment. As can be seen, the distance between confusion curve 408A of color 406D, and color 406E, of FIG. 4A is less than the distance between confusion curve 408A of color 406D, and color 406E, of FIG. 4C.

Turing now to FIG. 5, an exemplary user interface is provided illustrating conflict lines between selected colors in a color wheel, designated generally as user interface 500. User interface 500 is displayed via a user device, such as user devices 104A through 104C of FIG. 1. User interface 500 includes color wheel 502, colors 504A through 504F, and conflict lines 506A through 506C. Color wheel 502 may be associated with a color space, such as, for example, an HSV, HSL, HSB, Lab, LCh, Luv, HCL, or CIECAM color space.

As described herein, confusion lines and confusion curves highlight (e.g., identify) conflicts (and/or potential conflicts) between colors. By way of example, if a second color (e.g., 504B) intersects a curve of confusion of a first color (e.g., 504A), the intersection may indicate a color conflict between color 504A and color 504B. As noted throughout, color conflicts exist in varying severities based on factors, such as hue, saturation, contrast, and the like. For example, while two colors might fall along the same curve of confusion, thereby indicating a potential color conflict between the colors for a person with a particular CVD, the individual with the CVD may still be able to distinguish between the two colors (e.g., a dark red and a light green) depending on the additional factors, such as the saturation and lightness of the colors. Visually, and with respect to the intersection of a curve of confusion for a first color and a second color, the severity of a color conflict depends at least in part on the location of two colors (e.g., color 504A and color 504B) along the curve of confusion.

In some embodiments, severity can be determined using color contrast ratios (e.g., the ratio of the luminance of the brightest color to that of the darkest color). In other embodiments, severity can be determined using $\Delta E$ (e.g., dE, Delta-E), which, as described above, is the perceptual color difference between two colors (e.g., the visible difference, or error, between two colors mathematically). In some embodiments, CIE $\Delta E$ 2000 is used, however, as can be appreciated, other $\Delta E$ formulations may be used, such as, for example, CIE76, CIE94, and CMC I:c (1984).

In some embodiments, conflict lines 506A through 506C visually indicate that a conflict exists at a particular severity level between two selected colors in the color wheel. The thicker the conflict line, the greater the severity of the color conflict. Similarly, the thinner the conflict line, the lesser the severity of the color conflict. For example, conflict line 506A visually indicates a conflict at a particular severity level exists between color 504A and color 504B. As can be seen, conflict line 506A is thinner than conflict lines 506B and 506C, indicating the conflict between colors 504A and 504B is less severe than the conflicts between colors 504C and 504D, and 504E and 504F, respectively. Further, conflict line 506B visually indicates a conflict exists at another severity level between color 504C and color 504D. As can be seen, conflict line 506B is thicker than conflict line 506A and thinner than conflict line 506C, indicating the conflict between colors 504A and 504B is less severe than the conflict between color 504C and 504C, and the conflict between colors 504E and 504F is more severe than the conflict between color 504C and 504C. Further still, conflict line 506C visually indicates a conflict exists at yet another severity level between color 504E and color 504F. As can be seen, conflict line 506C is thicker than conflict lines 506A and 506B, indicating the conflict between colors 504E and 504F is more severe than the conflicts between colors 504A and 504B, and 504C and 504D, respectively.

While level of severity is indicated via line width, it should be appreciated that other visual indications may also be implemented to indicate conflict severity between colors. As can further be appreciated, and while not shown, conflict lines 506A, 506B, and 506C may also visually indicate a color conflict for a specific type of color vision deficiency.

Figure 6:
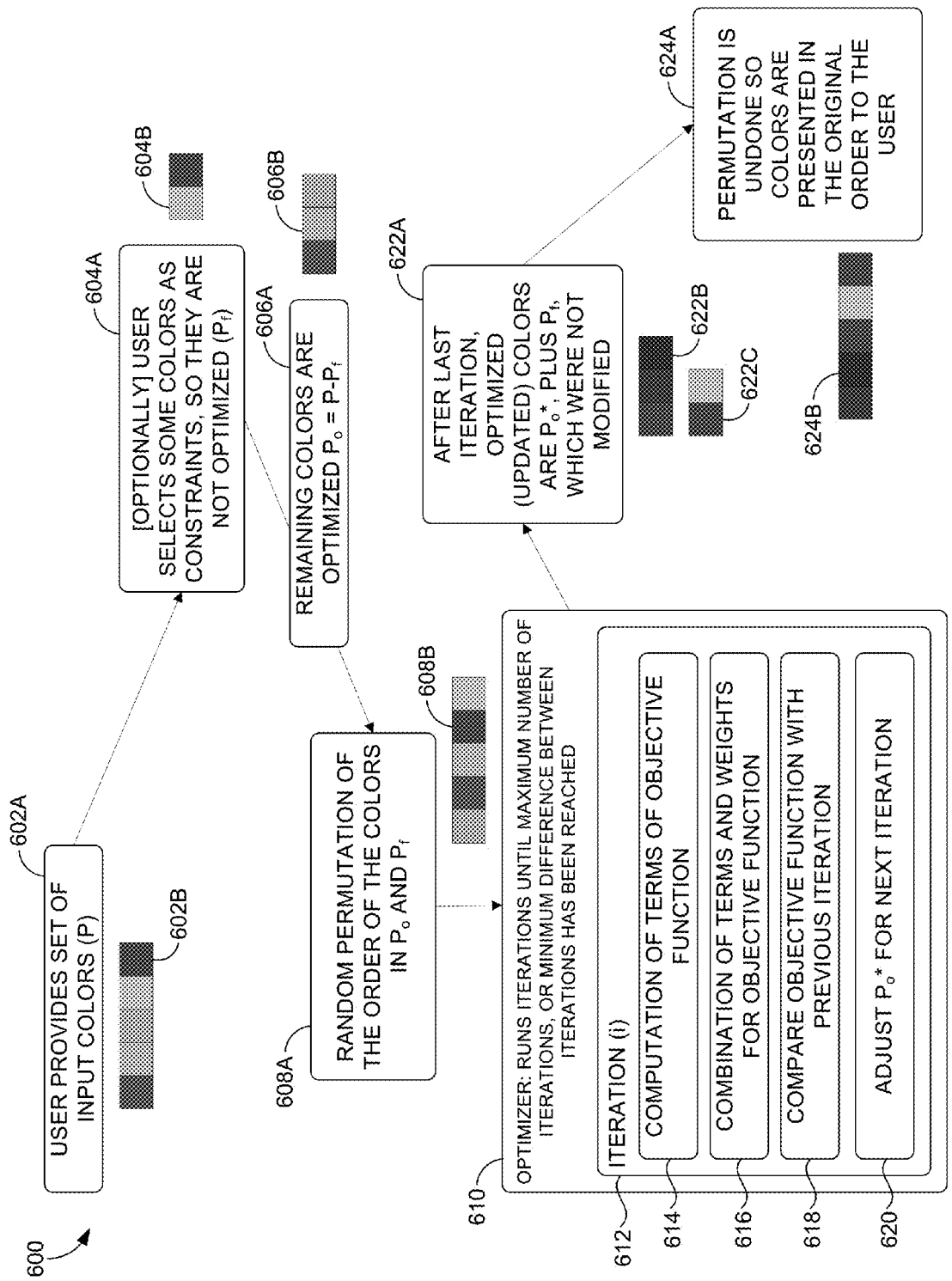
FIG. 6 is a schematic diagram showing an exemplary data flow for automatically optimizing for color accessibility, in accordance with embodiments of the present disclosure.

Turing now to FIG. 6, FIG. 6 is a schematic diagram showing an exemplary data flow for automatically optimizing for color accessibility (described further in conjunction with FIGS. 7 and 8), the data flow designated as data flow 600. Data flow 600 can be performed by an accessible color optimization engine, such as accessible color optimization engine 102 of FIG. 1. At block 602A, a user provides a set of input colors, such as input colors 602B (e.g., P). As described herein, the set of input colors may be an ordered or an unordered set of input colors, and may be provided to accessible color optimization engine 102. The user may provide the set of input colors via a color wheel. The user may additionally and/or alternatively provide the set of input colors by other means, such as, for example, providing the set of input colors in a list data structure stored in a data store. At block 604A, the user may provide color constraints, such as color constraints 604B. As described throughout, color constraints 604B (e.g., $P_f$) provided by the user may be associated with branding guidelines, and the like. In operation, color constraints indicate which colors from the set of input colors are not to be updated (e.g., will remain the same after optimization as they were prior to optimization). At block 606A, it is determined that the remaining colors 606B (e.g., $P_o$) not included in color constraints 604B are the colors to be optimized by the accessible color optimization engine 102.

Referring to block 608A, a random permutation of the set of colors is determined, such as permutation 608B, and at blocks 610 through 620, the objective function described herein above is evaluated on permutation 608B. In some embodiment, because the objective function is evaluated on permutation 608B sequentially (e.g., one color at a time), the resulting output (e.g., the set of input colors including an updated plurality of updatable colors) may differ for each permutation of the set of input colors on which the objective function is evaluated. In other words, each resulting output set of accessible colors generated using a different permutation of the set of input colors (such as permutation 608B of input colors 602B) is a different valid solution for the set of input colors (e.g., a different result optimized for color accessibility). Advantageously, in a content generation context, having more than one valid solution (e.g., set of colors optimized for accessibility) is more user friendly to a user (e.g., content creator).

Specifically with respect to block 612, the objective function described herein is iteratively evaluated on permutation 608B. At block 614, for each iteration of the objective function, the terms of the objective function are computed (e.g., the CVD alignment term, the out-of-gamut term, the distinguishability term, and the faithfulness term). At block 616, the terms (and their respective weights as described herein) are then combined to determine an accessibility value. At block 618, the accessibility value is compared to accessibility values of previous iterations. At block 620, the color in the set of input colors on which the objective is being evaluated is adjusted, and the steps designated by blocks 614 through 618 are repeated until the set of colors including the plurality of updatable colors is optimized.

At block 622A, the objective function evaluated on the set of input colors results in an updated plurality of updatable colors 622B and the color constraints 622C (e.g., 604B). At block 624A, the updated plurality of updatable colors 622B and the color constraints 622C are reordered into their original order (e.g., order associated with input colors 602B) and the optimized (e.g., updated) set of accessibility colors 624B is presented to the user on a graphical user interface, such as a graphical user interface of a user device. As can be seen, the optimized (e.g., updated) set of accessibility colors 624B is the optimized set of colors based on input colors 602B.

Figure 7:
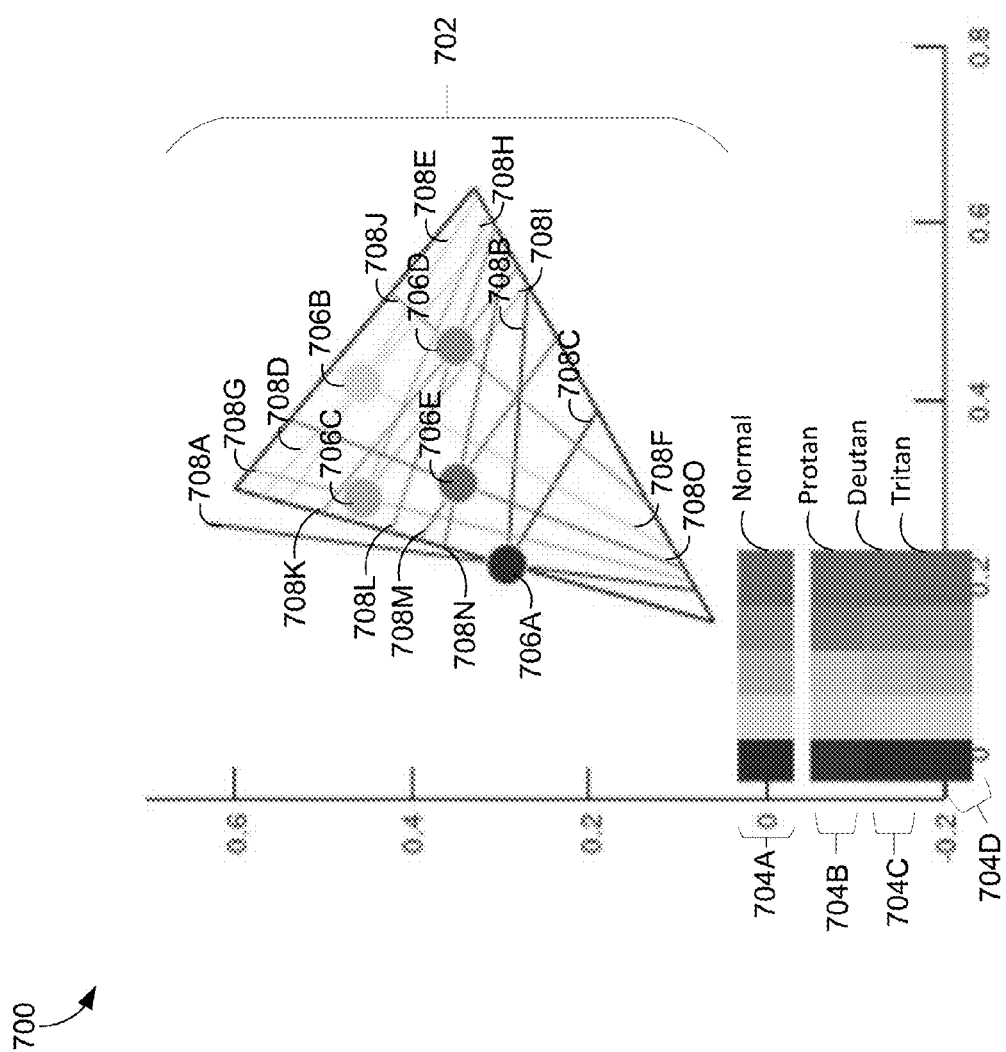
FIG. 7 is a schematic diagram showing an exemplary user interface illustrating a set of input colors in an sRGB color space, in accordance with embodiments of the present disclosure.

Turing now to FIG. 7, an exemplary user interface is provided illustrating a set of input colors in an sRGB color space (e.g., gamut), that can be optimized using a lines of confusion accessibility optimization manager, such as lines of confusion accessibility optimization manager 204 of FIG. 2. The user interface provided is designated generally as user interface 700. The user interface 700 is displayed via a user device, such as user devices 104A through 104C of FIG. 1. The user interface 700 includes color space 702, color palettes 704A through 704D, colors 706A through 706E, and lines of confusion 708A through 708O. Color space 702 maybe associated with a variety of color gamuts, such as, for example, an sRGB, and/or P3 color gamut. Color palette 704A visually indicates how colors 706A through 706E are visually perceived for someone without a vision impairment. Color palette 704B visually indicates how colors 706A through 706E are visually perceived for someone with a protan CVD vision impairment. Color palette 704C visually indicates how colors 706A through 706E are visually perceived for someone with a deutan CVD vision impairment. Color palette 704D visually indicates how colors 706A through 706E are visually perceived for someone with a tritan CVD vision impairment.

Colors 706A through 706E are associated with a selection of a set of input colors used to automate color optimization. As described above in connection with FIG. 6, lines of confusion 708A through 708C associated with color 706A visually indicate confusions of colors for various CVDs associated with color 706A. Lines of confusion 708D through 708F associated with color 706B visually indicate confusions of colors for various CVDs associated with color 706B. Lines of confusion 708G through 708I associated with color 706C visually indicate confusions of colors for various CVDs associated with color 706C. Lines of confusion 708J through 708L associated with color 706D visually indicate confusions of colors for various CVDs associated with color 706D. Lines of confusion 708M through 708O associated with color 706E visually indicate confusions of colors for various CVDs associated with color 706E. As described throughout, when a line of confusion (e.g., 708A) for a color (e.g., 706A) intersects another color (e.g., 706B) a color conflict exists between the two colors for a person with the CVD associated with the intersecting line of confusion.

As described herein above, an objective function may be evaluated on colors 706A through 706E to automatically optimize them for color accessibility. In some embodiments, colors 706B and 706D may be associated with a color constraint (e.g., will remain the same after accessibility optimization).

Figure 8B:
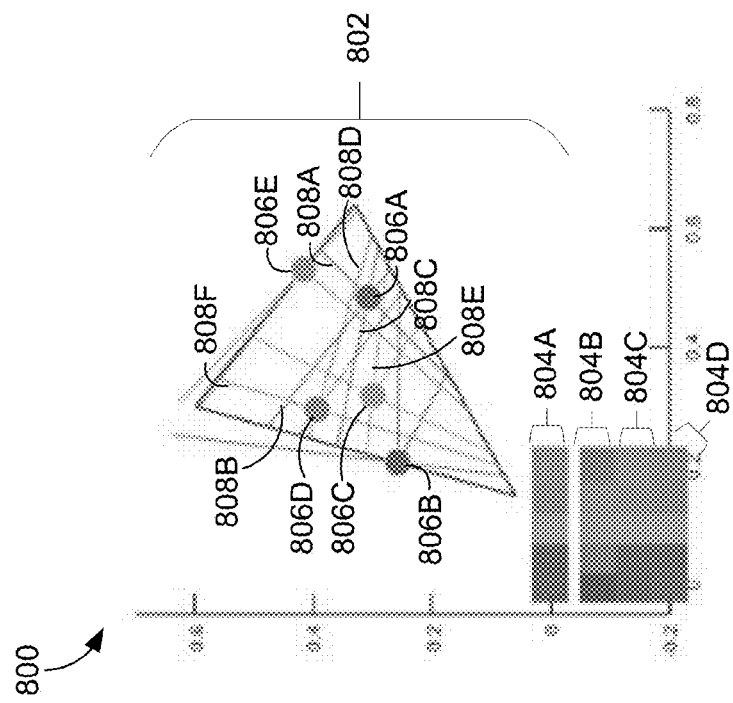
FIGS. 8A-8B are schematic diagrams showing exemplary user interfaces illustrating the automatic optimization of colors utilizing an objective function in an sRGB color space, in accordance with embodiments of the present disclosure.
Figure 8A:
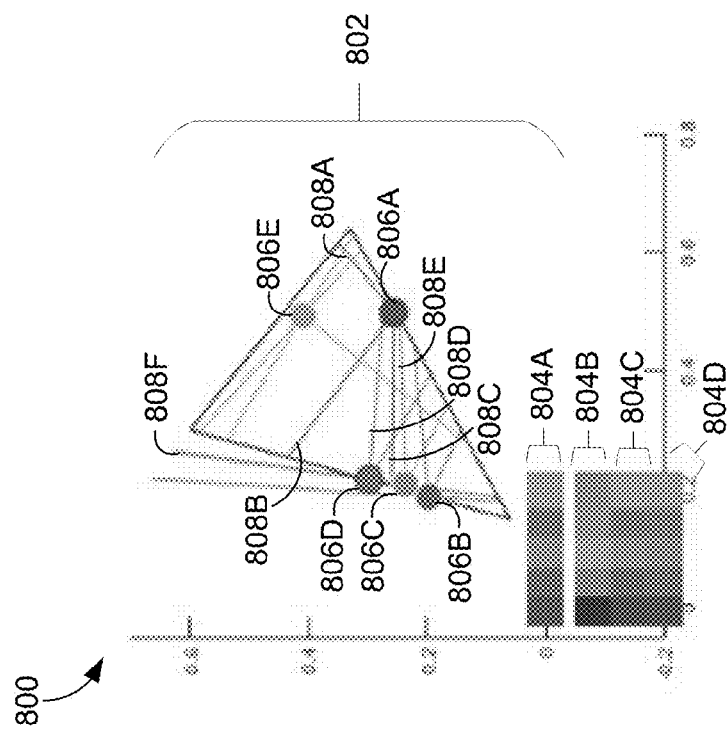

Turing now to FIGS. 8A-8B, exemplary user interfaces are provided illustrating the automatic optimization of colors utilizing an objective function in an sRGB color space. As can be seen, while FIG. 7 illustrates a set of input colors inside an sRGB color gamut, that can be optimized using a lines of confusion accessibility optimization manager, FIGS. 8A and 8B illustrate the automatic optimization of colors from FIG. 8A to FIG. 8B utilizing an objective function. For each of FIGS. 8A through 8B, the user interface is designated as user interface 800. User interface 800 is displayed via a user device, such as user devices 104A through 104C of FIG. 1. User interface 800 includes color space 802, color palettes 804A through 804D, colors 806A through 806E, and lines of confusion 808A through 808F. Color palette 804A visually indicates how colors 806A through 806E are visually perceived for someone without a vision impairment. Color palette 804B visually indicates how colors 806A through 806E are visually perceived for someone with a protan CVD vision impairment. Color palette 804C visually indicates how colors 806A through 806E are visually perceived for someone with a deutan CVD vision impairment. Color palette 804D visually indicates how colors 806A through 806E are visually perceived for someone with a tritan CVD vision impairment. Colors 806A through 806E are associated with a selection of a set of input colors used to automate color optimization.

Lines of confusion 808A through 808C are associated with color 806A. Lines of confusion 808D and 808F are associated with color 806D. Line of confusion 808E is associated with color 806C. As descried herein, lines of confusion may visually indicate confusions of colors between two colors for a particular type of CVD.

With respect to FIG. 8A, colors 806A through 806E correspond to a set of input colors. As visually indicated in color space 802 of FIG. 8A, a color conflict exists between color 806A and color 806D as line of confusion 808D associated with color 806D intersects color 806A. Similarly, as visually indicated in color space 802 of FIG. 8A, a color conflict exists between color 806A and color 806C as line of confusion 808C associated with color 806A intersects color 806C, and line of confusion 808E associated with color 806C intersects color 806E. Similarly still, as visually indicated in color space 802 of FIG. 8A, a color conflict exists between color 806D, color 806C, and color 806B, as line of confusion 808F associated with color 806D intersects colors 806C and 806B.

As described herein in connection with FIG. 6 and elsewhere, an objective function may be evaluated on the set of input colors resulting in an updated set of input colors that are color accessible. With respect to FIG. 8B, colors 806A through 806E visually indicate an updated set of input colors after the objective function has been evaluated on the set of input colors in FIG. 8A. As indicated in color space 802 of FIG. 8B, post-accessibility optimization, no color conflict exists between color 806A and color 806D, between color 806A and 806C, or among color 806D, color 806C, and color 806B (e.g., no lines of confusion for a color intersect with another color).

Example Flow Diagrams

With reference to FIGS. 9, 10, 11, and 12, flow diagrams are provided illustrating methods for optimizing accessible color themes. The methods may be performed using the accessible color optimization engine 200 of FIG. 2 as described herein. In embodiments, one or more computer storage media having computer-executable instructions embodied thereon that, when executed, by one or more processors, can cause the one or more processors to perform the methods described below.

Figure 9:
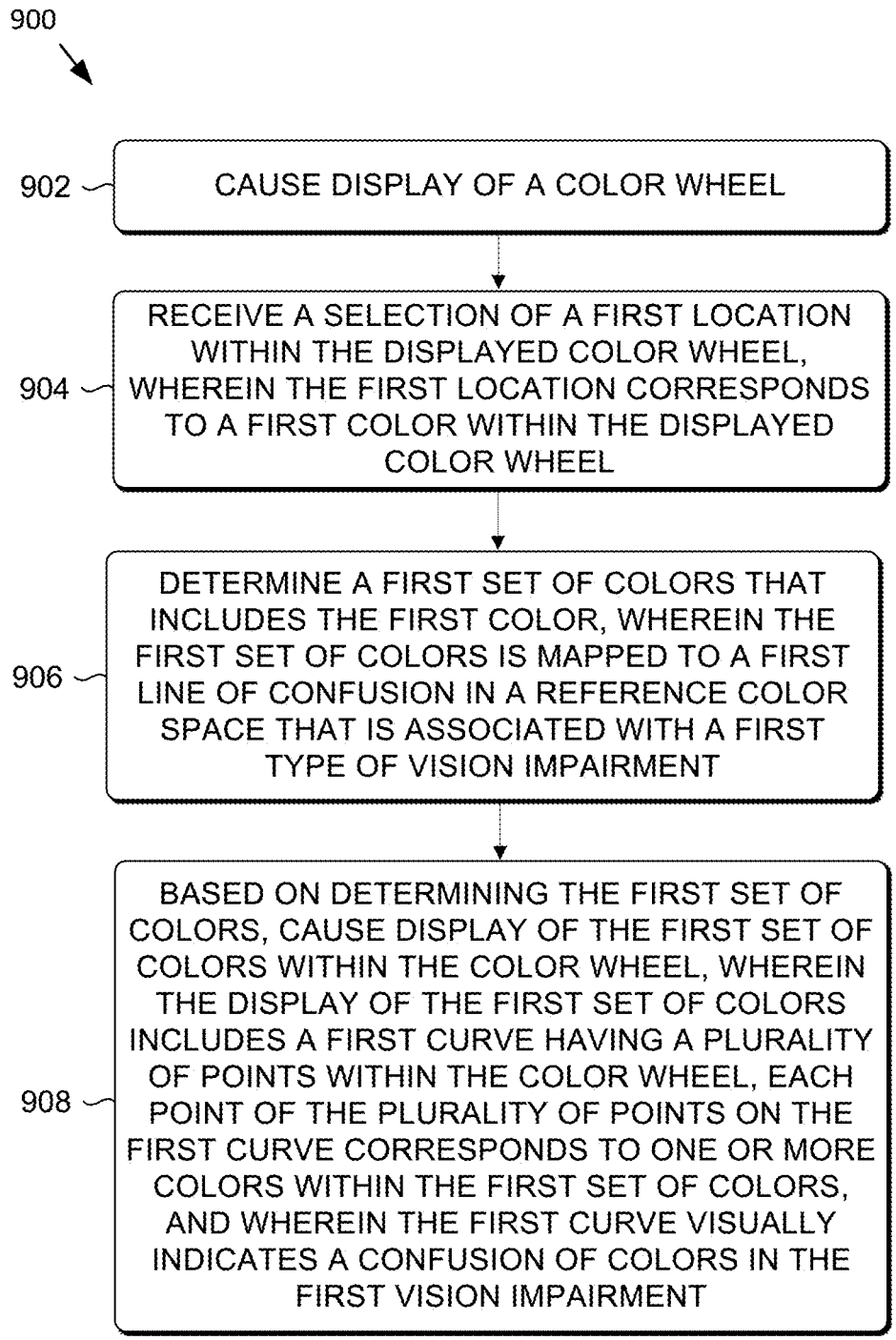
FIG. 9 is a flow diagram showing an example method for displaying curves of confusion on a color wheel, in accordance with embodiments of the present disclosure.

Turing now to FIG. 9, a flow diagram is provided showing an example method 900 for displaying curves of confusion on a color wheel, in accordance with embodiments of the present disclosure (and described further in conjunction with FIGS. 1 through 5). In embodiments, method 900 is performed by a curves of confusion accessibility optimization manager, such as curves of confusion accessibility optimization manager 202 of accessibility color optimization engine 200 of FIG. 2. Initially, at block 902, a color wheel is displayed, such as on a graphical user interface of a user device, such as user devices 104A through 104C of FIG. 1. In embodiments, the color wheel can represent a color picker, and may be associated with any number of color spaces, such as an HSV, HSL, HSB, Lab, LCh, Luv, HCL, or CIECAM color space. At block 904, a selection of a first location within the color wheel is received. The first location corresponds to a first color within the color wheel. At block 906, a first set of colors is determined that includes the first color, where the determined first set of colors is mapped to a first line of confusion in a color space that is associated with a first type of vision impairment. Here, the color space may be a CIE xyY color space. A first type of vision impairment may include a CVD, such as protan, deutan, and/or tritan. Referring to block 908, the first set of colors is displayed in a color wheel where the display of the first set of colors includes a first curve. The first curve includes a plurality of points within the color wheel, where each point of the plurality of points on the first curve corresponds to one or more colors within the first set of colors. The first curve visually indicates a confusion of colors in the first vision impairment.

Figure 10:
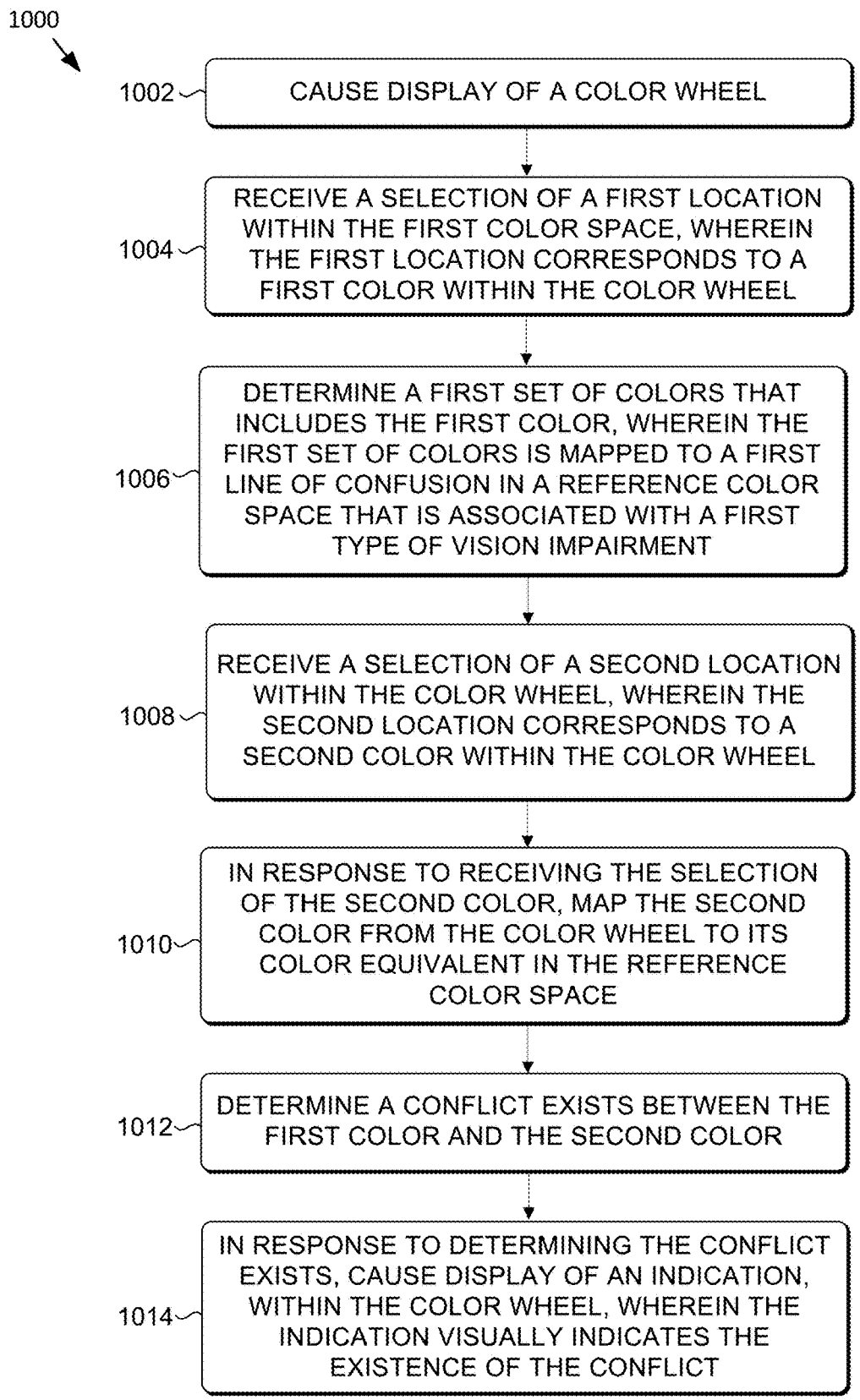
FIG. 10 is a flow diagram showing an example method for indicating a conflict exists between colors on a color wheel, in accordance with embodiments of the present disclosure.

Turing now to FIG. 10, a flow diagram is provided showing an example method 1000 for indicating a conflict exists between colors on a color wheel, in accordance with embodiments of the present disclosure (and described further in conjunction with FIGS. 1 through 5). In embodiments, method 1000 is performed by a curves of confusion accessibility optimization manager, such as curves of confusion accessibility optimization manager 202 of accessibility color optimization engine 200 of FIG. 2. Initially, at block 1002 a color wheel is displayed, such as on a graphical user interface of a user device, such as user devices 104A through 104C of FIG. 1. In embodiments, the color wheel may be associated with a color picker. The color wheel may further be associated with any number of color spaces, such as an HSV, HSL, HSB, Lab, LCh, Luv, HCL, or CIECAM color space. At block 1004 a selection of a first location within the color wheel is received. Here, the first location corresponds to a first color within the color wheel. Referring to block 1006 a first set of colors in a reference color space that includes the first color is determined. Here the first set of colors is mapped to a first line of confusion in the reference color space. The first line of confusion is associated with a first type of vision impairment. The first type of vision impairment may include, for example, include a CVD, such as protan, deutan, and/or tritan. At block 1008 a selection of a second location within the color wheel is received. The second location corresponds to a second color within the color wheel. Turing to block 1010 in response to receiving the selection of the second color, the second color is mapped from the color wheel to its color equivalent in the reference color space. At block 1012 a conflict is determined to exist between the first color and the second color. At block 1014 in response to determining that the conflict exists, an indication is displayed within the color wheel that visually indicates the existence of the conflict.

Figure 11:
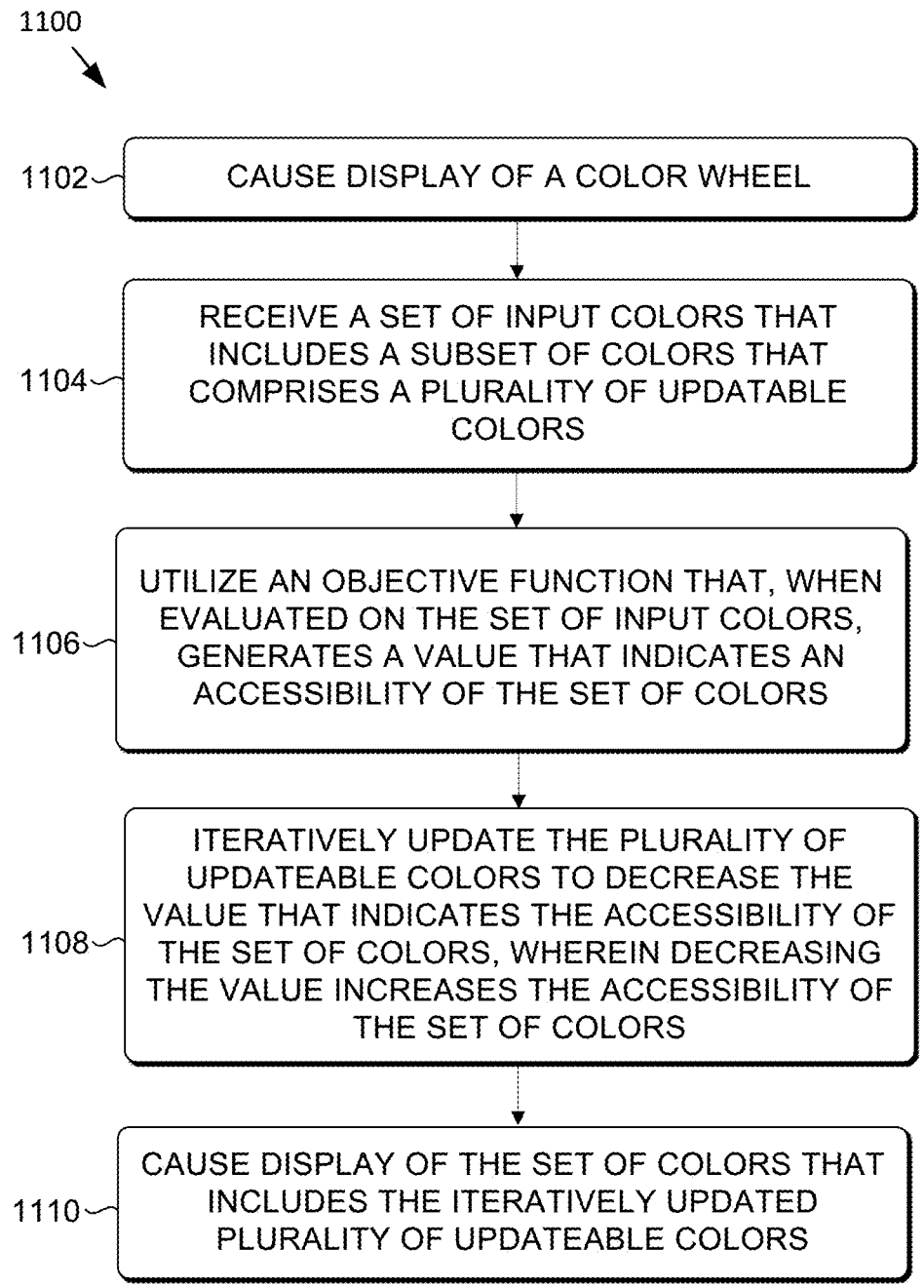
FIG. 11 is a is a flow diagram showing an example method for automatically optimizing a set of input colors for accessibility, in accordance with embodiments of the present disclosure.

Turing now to FIG. 11, a flow diagram is provided showing an example method 1100 for automatically optimizing a set of input colors for accessibility, in accordance with embodiments of the present disclosure (and described further in conjunction with FIGS. 6 through 8). In embodiments, method 1100 is performed by a lines of confusion accessibility optimization manager, such as lines of confusion accessibility optimization manager 204 of accessibility color optimization engine 200 of FIG. 2. Initially, at block 1102 a color wheel is displayed, such as on a graphical user interface of a user device, such as user devices 104A through 104C of FIG. 1. In embodiments, the color wheel can represent a color picker, and may be associated with any number of color spaces, such as, for example, an HSV, HSL, HSB, Lab, LCh, Luv, HCL, or CIECAM color space. At block 1104 a set of input colors that includes a subset of colors that comprises a plurality of updatable colors is received. Referring to block 1106 an objective function is utilized on the set of input colors generate a value that indicates an accessibility of the set of colors. The objective function may include at least one of a CVD alignment term, an out-of-gamut term, a distinguishability term, and a faithfulness term. At block 1108 the plurality of updateable colors is iteratively updated to decrease the value that indicates the accessibility of the set of colors. At block 1110 the set of colors that includes the iteratively updated plurality of updateable colors is displayed.

Figure 12:
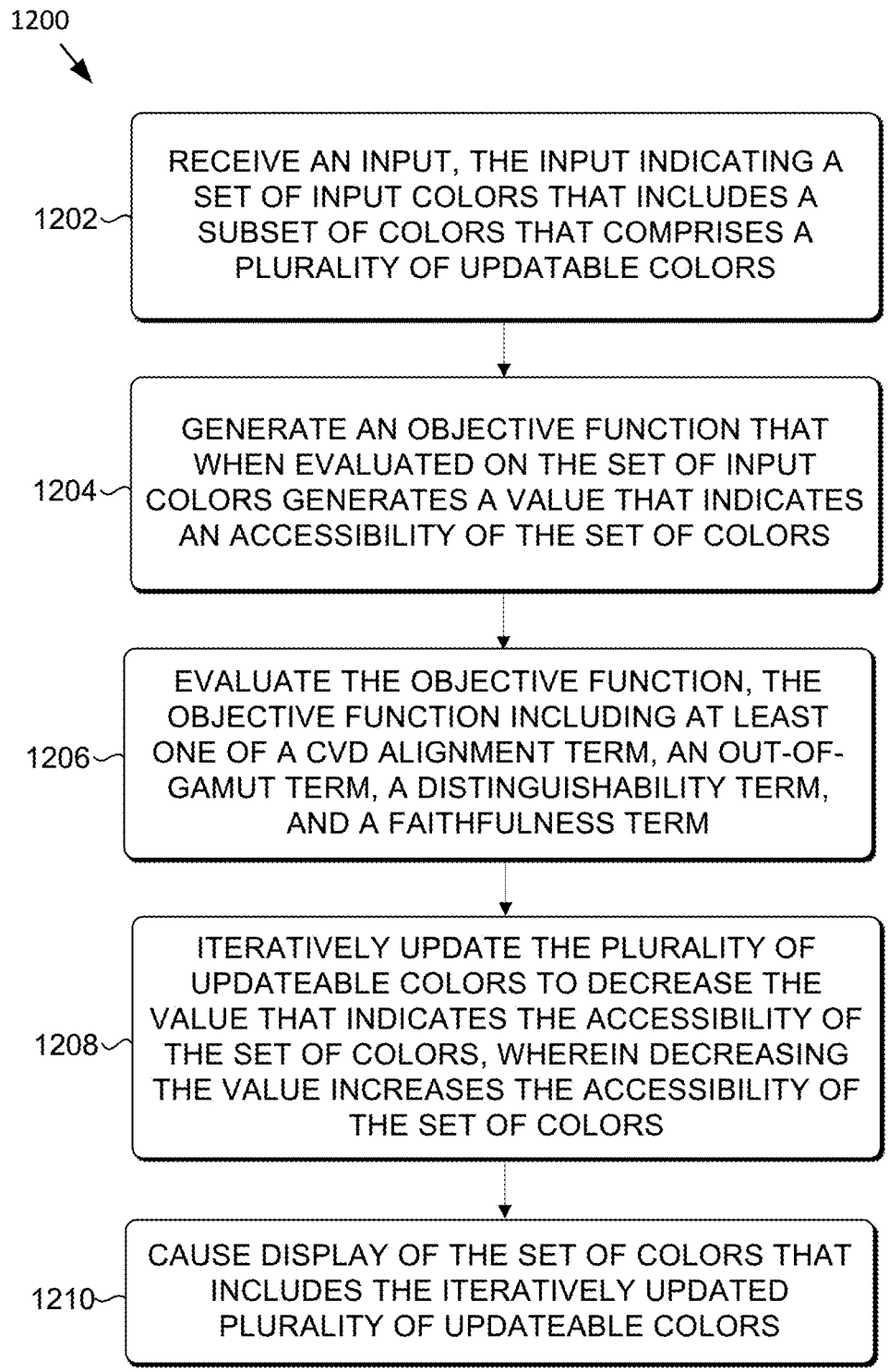
FIG. 12 is a flow diagram showing an example method for optimizing a set of input colors for accessibility automatically, in accordance with embodiments of the present disclosure.

Turning now to FIG. 12, a flow diagram is provided showing an example method 1200 for optimizing a set of input colors for accessibility automatically, in accordance with embodiments of the present disclosure (and described further in conjunction with FIGS. 6 through 8). In embodiments, method 1200 is performed by a lines of confusion accessibility optimization manager, such as lines of confusion accessibility optimization manager 204 of accessibility color optimization engine 200 of FIG. 2. Initially, at block 1202 an input indicating a set of input colors is received. Here, the set of input colors includes a subset of colors that comprises a plurality of updateable colors. At block 1206 an objective function is generated. When evaluated on the set of input colors, the objective function generates a value that indicates an accessibility of the set of colors. The objective function may include at least one of a CVD alignment term, an out-of-gamut term, a distinguishability term, and a faithfulness term. Turing to block 1208 the plurality of updateable colors is iteratively updated to decrease the value that indicates the accessibility of the set of colors. Here, decreasing the value increases the accessibility of the set of colors (e.g., an inverse relationship). Referring to block 1210 the set of colors that includes the iteratively updated set of updateable colors is displayed.

Exemplary Operating Environment

Figure 13:
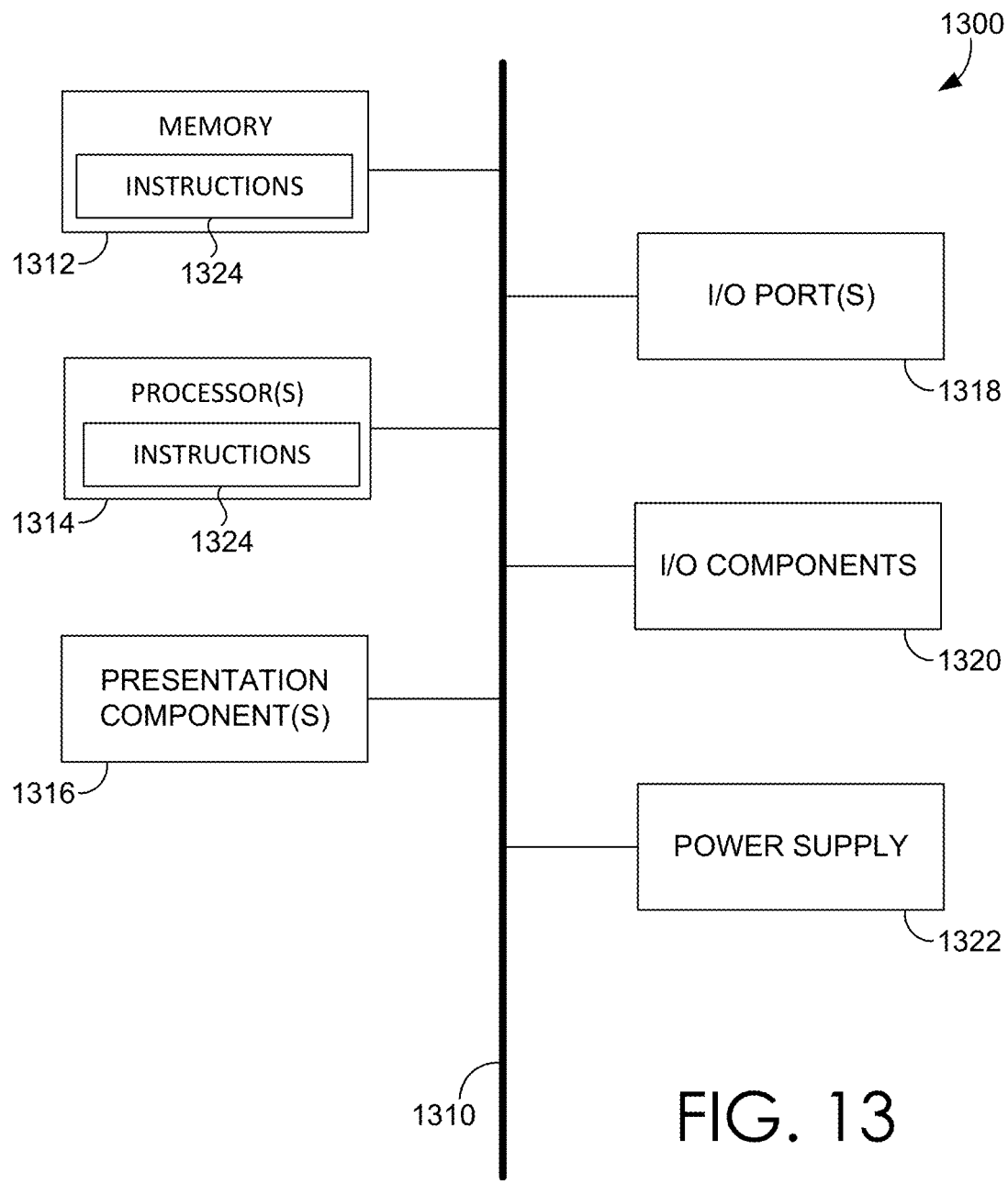
FIG. 13 is a block diagram of an exemplary computing environment suitable for use in implementing embodiments of the present disclosure.

Having described an overview of embodiments of the present invention, an exemplary operating environment in which embodiments of the present invention may be implemented is described below in order to provide a general context for various aspects of the present invention. Referring now to FIG. 13 in particular, an exemplary operating environment for implementing embodiments of the present invention is shown and designated generally as computing device 1300. Computing device 1300 is but one example of a suitable computing environment and is not intended to suggest any limitation as to the scope of use or functionality of the invention. Neither should computing device 1300 be interpreted as having any dependency or requirement relating to any one or combination of components illustrated.

The invention may be described in the general context of computer code or machine-useable instructions, including computer-executable instructions such as program modules, being executed by a computer or other machine, such as a cellular telephone, personal data assistant or other handheld device. Generally, program modules including routines, programs, objects, components, data structures, etc., refer to code that perform particular tasks or implement particular abstract data types. The invention may be practiced in a variety of system configurations, including hand-held devices, consumer electronics, general-purpose computers, more specialty computing devices, etc. The invention may also be practiced in distributed computing environments where tasks are performed by remote-processing devices that are linked through a communications network.

With reference to FIG. 13, computing device 1300 includes bus 1310 that directly or indirectly couples the following devices: memory 1312, one or more processors 1314, one or more presentation components 1316, input/output (I/O) ports 1318, input/output components 1320, and illustrative power supply 1322. Bus 1310 represents what may be one or more busses (such as an address bus, data bus, or combination thereof). Although the various blocks of FIG. 13 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventor recognizes that such is the nature of the art, and reiterates that the diagram of FIG. 13 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 13 and reference to "computing device."

Computing device 1300 typically includes a variety of computer-readable media. Computer-readable media can be any available media that can be accessed by computing device 1300 and includes both volatile and nonvolatile media, and removable and non-removable media. By way of example, and not limitation, computer-readable media may comprise computer storage media and communication media.

Computer storage media includes both volatile and non-volatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 1300. Computer storage media does not comprise signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 1312 includes computer-storage media in the form of volatile and/or nonvolatile memory. The memory may be removable, non-removable, or a combination thereof. Exemplary hardware devices include solid-state memory, hard drives, optical-disc drives, etc. Computing device 1300 includes one or more processors that read data from various entities such as memory 1312 or I/O components 1320. Presentation component(s) 1316 present data indications to a user or other device. Exemplary presentation components include a display device, speaker, printing component, vibrating component, etc.

I/O ports 1318 allow computing device 1300 to be logically coupled to other devices including I/O components 1320, some of which may be built in. Illustrative components include a microphone, joystick, game pad, satellite dish, scanner, printer, wireless device, etc. The I/O components 1320 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of computing device 1300.

Computing device 1300 may be equipped with depth cameras, such as stereoscopic camera systems, infrared camera systems, RGB camera systems, touchscreen technology, and combinations of these, for gesture detection and recognition. Additionally, the computing device 1300 may be equipped with accelerometers or gyroscopes that enable detection of motion. The output of the accelerometers or gyroscopes may be provided to the display of computing device 1300 to render immersive augmented reality or virtual reality.

Embodiments described herein facilitate authoring and optimization of accessible color themes based on leveraging the use of confusion lines to identify and highlight relationships between colors that may be inaccessible (e.g., indistinguishable) for a person with a vision impairment, such as a color vision deficiency. Components described herein refer to integrated components of accessible color optimization system. The integrated components refer to the hardware architecture and software framework that support functionality using the accessible color optimization system. The hardware architecture refers to physical components and interrelationships thereof, and the software framework refers to software providing functionality that can be implemented with hardware embodied on a device.

The accessible color optimization system can operate within the system components to operate computer hardware to provide system functionality. At a low level, hardware processors execute instructions selected from a machine language (also referred to as machine code or native) instruction set for a given processor. The processor recognizes the native instructions and performs corresponding low level functions relating, for example, to logic, control and memory operations. Low level software written in machine code can provide more complex functionality to higher levels of software. As used herein, computer-executable instructions includes any software, including low level software written in machine code, higher level software such as application software and any combination thereof. In this regard, the system components can manage resources and provide services for the system functionality. Any other variations and combinations thereof are contemplated with embodiments of the present invention.

Having identified various components in the present disclosure, it should be understood that any number components and arrangements may be employed to achieve the desired functionality within the scope of the present disclosure. For example, the components in the embodiments depicted in the figures are shown with lines for the sake of conceptual clarity. Other arrangements of these and other components may also be implemented. For example, although some components are depicted as single components, many of the elements described herein may be implemented as discrete or distributed components or in conjunction with other components, and in any suitable combination and location. Some elements may be omitted altogether.

Moreover, various functions described herein as being performed by one or more entities may be carried out by hardware, firmware, and/or software, as described below. For instance, various functions may be carried out by a processor executing instructions stored in memory. As such, other arrangements and elements (e.g., machines, interfaces, functions, orders, and groupings of functions, etc.) can be used in addition to or instead of those shown.

The subject matter of embodiments of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

For purposes of this disclosure, the word "including" has the same broad meaning as the word "comprising," and the word "accessing" comprises "receiving," "referencing," or "retrieving." Further the word "communicating" has the same broad meaning as the word "receiving," or "transmitting" facilitated by software or hardware-based buses, receivers, or transmitters" using communication media described herein. Also, the word "initiating" has the same broad meaning as the word "executing or "instructing" where the corresponding action can be performed to completion or interrupted based on an occurrence of another action. In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

For purposes of a detailed discussion above, embodiments of the present invention are described with reference to a distributed computing environment; however the distributed computing environment depicted herein is merely exemplary. Components can be configured for performing novel aspects of embodiments, where the term "configured for" can refer to "programmed to" perform particular tasks or implement particular abstract data types using code. Further, while embodiments of the present invention may generally refer to the search system and the schematics described herein, it is understood that the techniques described may be extended to other implementation contexts.

Embodiments of the present invention have been described in relation to particular embodiments which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects hereinabove set forth together with other advantages which are obvious and which are inherent to the structure.

It will be understood that certain features and sub-combinations are of utility and may be employed without reference to other features or sub-combinations. This is contemplated by and is within the scope of the claims.

What is claimed is:

1. A computer implemented method, the method comprising:
receiving a selection of a first location from within a color space displayed on an interface, wherein the first location corresponds to a first color within the color space;
determining a first set of colors that includes the first color, wherein the first set of colors is mapped in a reference color space to a first line of confusion that is associated with a first type of vision impairment;
receiving a selection of a second location from within the color space displayed on the interface, wherein the second location corresponds to a second color within the color space;
in response to receiving the selection of the second color, mapping the second color from the color space displayed on the interface to its color equivalent in the reference color space;
determining a conflict exists between the first color and the second color, based at least in part on the first line of confusion; and
in response to determining the conflict exists, causing display of an indication, within the color space displayed on the interface, wherein the indication visually indicates existence of the conflict.

2. The method of claim 1, wherein mapping the second color from the color space to its color equivalent in the reference color space is based on applying a color transformation to chromaticity coordinates associated with the second color in the color space.

3. The method of claim 1, wherein the color space is associated with one of an HSV, HSL, HSB, Lab, LCh, Luv, HCL, or CIECAM color space.

4. The method of claim 1, wherein the reference color space is a CIE xyY color space.

5. The method of claim 1, further comprising:
based on determining the conflict exists between the first color and the second color, determining a third color within the color space such that no conflict exists between the first color and the third color; and
causing display of the third color as a recommendation, wherein a selection of the third color replaces the selection of the second color.

6. The method of claim 1, further comprising:
causing a display of the first set of colors of the first line of confusion as a first curve on the color space, wherein the first curve visually indicates a confusion of colors in the first type of vision impairment.

7. The method of claim 6, further comprising:
in response to receiving an input to reposition the first color in the first location to an alternative location corresponding to an alternative color within the color space, iteratively updating the first curve to visually indicate an updated confusion of colors in the first type of vision impairment, wherein iteratively updating the first curve is based on determining an alternative set of colors that includes the alternative color, wherein the alternative set of colors is mapped to an alternative line of confusion in the reference color space associated with the first type of vision impairment.

8. A system comprising:
a memory component; and
one or more processing devices coupled to the memory component, the one or more processing devices to perform operations comprising:
receiving a selection of a first location from within a color space displayed on an interface, the first location corresponding to a first color within the color space;
determining, in a reference color space, a first set of colors that includes the first color based on mapping the first color to a first line of confusion that is associated with a first type of vision impairment;
receiving a selection of a second location from within the color space displayed on the interface, the second location corresponding to a second color within the color space;
mapping the second color to a color equivalent of the second color in the reference color space;
determining a conflict exists between the first color and the second color based on the mapping of the first color to the first line of confusion and the mapping of the second color to the color equivalent; and
in response to determining the conflict exists, causing a visual indication of existence of the conflict within a display of the color space on the interface.

9. The system of claim 8, wherein mapping the second color from the color space to the color equivalent in the reference color space is based on applying a color transformation to chromaticity coordinates associated with the second color in the color space.

10. The system of claim 8, wherein the color space is associated with one of an HSV, HSL, HSB, Lab, LCh, Luv, HCL, or CIECAM color space.

11. The system of claim 8, wherein the reference color space is a CIE xyY color space.

12. The system of claim 8, the operations further comprising:
based on determining the conflict exists between the first color and the second color, determining a third color within the color space such that no conflict exists between the first color and the third color; and
causing display of the third color as a recommendation, wherein a selection of the third color replaces the selection of the second color.

13. The system of claim 8, the operations further comprising:
causing display of the first set of colors of the first line of confusion as a first curve on the color space, wherein the first curve visually indicates a confusion of colors in the first type of vision impairment.

14. The system of claim 13, the operations further comprising:
in response to receiving an input to reposition the first color to an alternative color within the color space, iteratively updating the first curve to visually indicate an updated confusion of colors in the first type of vision impairment, wherein iteratively updating the first curve is based on determining an alternative set of colors that includes the alternative color, wherein the alternative set of colors is mapped to an alternative line of confusion in the reference color space associated with the first type of vision impairment.

15. One or more computer storage media storing computer-useable instructions that, when executed by one or more computing devices, causes the one or more computing devices to perform operations, the operations comprising:
receiving a selection of a first color within a displayed color space;
mapping the first color to a first line of confusion comprising a first set of colors in a reference color space, the first line of confusion associated with a first type of vision impairment;
causing a display of the first line of confusion as a first curve on the displayed color space, wherein the first curve visually indicates a confusion of colors in the first type of vision impairment;
determining a second set of colors that includes the first color, wherein the second set of colors is mapped to a second line of confusion in the reference color space, the second line of confusion associated with a second type of vision impairment;
determining a third set of colors that includes the first color, wherein the third set of colors is mapped to a third line of confusion in the reference color space, the third line of confusion associated with a third type of vision impairment; and
based on determining each of the second set of colors and the third set of colors, causing display of each of the second set of colors and the third set of colors within the color space, wherein the display of the second set of colors includes a second curve within the color space that visually indicates a confusion of colors in the second type of vision impairment, and display of the third set of colors includes a third curve within the color space that visually indicates a confusion of colors in the third type of vision impairment.

16. The one or more computer storage media of claim 15, the operations further comprising:
based on receiving the selection of the first color, transforming the first color within the displayed color space into a color equivalent of the first color in the reference color space, wherein the transforming is based on applying a color transformation to chromaticity coordinates associated with the first color.

17. The one or more computer storage media of claim 15, the operations further comprising:
in response to receiving an input to reposition the first color to an alternative location corresponding to an alternative color within the color space, iteratively updating the first curve to visually indicate an updated confusion of colors in the first type of vision impairment, wherein updating the first curve is based on determining an alternative set of colors that includes the alternative color, wherein the alternative set of colors is mapped to an alternative line of confusion in the reference color space associated with the first type of vision impairment.

* * * * *